(12) United States Patent
Burrow et al.

(10) Patent No.: US 7,178,521 B2
(45) Date of Patent: Feb. 20, 2007

(54) ADJUSTABLE LENGTH BREATHING CIRCUIT

(75) Inventors: Kevin D. Burrow, Fishers, IN (US); Dennis Irlbeck, Noblesville, IN (US); Thomas W. McGrail, Cicero, IN (US); Bart H. Burrow, Noblesville, IN (US); Michael G. Mitchell, Pendleton, IN (US); David L. Richards, Elwood, IN (US)

(73) Assignee: King Systems Corporation, Noblesville, IN (US)

( * ) Notice: Subject to any disclaimer, the term of this patent is extended or adjusted under 35 U.S.C. 154(b) by 0 days.

(21) Appl. No.: 10/811,121

(22) Filed: Mar. 26, 2004

(65) Prior Publication Data

US 2005/0150505 A1   Jul. 14, 2005

Related U.S. Application Data

(60) Provisional application No. 60/535,235, filed on Jan. 9, 2004.

(51) Int. Cl.
 *A62B 9/04*   (2006.01)
 *A61M 16/00*  (2006.01)
(52) U.S. Cl. .......................... 128/202.27; 128/207.18; 128/911
(58) Field of Classification Search .......... 128/204.18, 128/204.24, 204.25, 202.27, 205.12, 205.27, 128/205.17, 205.29, 204.22, 204.26, 206.15, 128/207.14, 911, 912, 910, 914, DIG. 26, 128/207.15, 207.16, 204.16
See application file for complete search history.

(56) References Cited

U.S. PATENT DOCUMENTS 876,766 A    1/1908 Blaisdell
(Continued)

FOREIGN PATENT DOCUMENTS

EP    81304018.5    2/1981
(Continued)

OTHER PUBLICATIONS

Andrews, J. Jeffrey, *Inhaled Anesthetic Delivery*, Anesthesia, Fourth Edition, pp. 185; and 203-207.

(Continued)

*Primary Examiner*—Teena K. Mitchell
(74) *Attorney, Agent, or Firm*—E. Victor Indiano; Indiano Vaughan LLP

(57) ABSTRACT

A unilimb breathing circuit has a proximal end coupling member, a distal end coupling member, an expiratory tube extending between the proximal and distal end coupling members, and an inspiratory tube extending between the proximal and distal end coupling members. The expiratory tube is a corrugated expiratory tube that is expandable between a fully compressed rest position, and a fully expanded rest position, and has a plurality of intermediate rest positions. At the plurality of intermediate rest positions, the expiratory tube is capable of maintaining its rest length without the exertion of an external force. The inspiratory tube is a corrugated inspiratory tube having a length that is variable between a fully compressed rest position and a fully expanded rest position, and includes a plurality of intermediate rest positions between the fully expanded rest position and the fully compressed rest position. The inspiratory tube is also capable of maintaining these intermediate rest positions without the exertion of an external force.

22 Claims, 12 Drawing Sheets

U.S. PATENT DOCUMENTS

| | | | |
|---|---|---|---|
| 1,148,093 A | 7/1915 | Kells | |
| 1,755,151 A | 4/1930 | Henderson | |
| 1,994,091 A | 3/1935 | Shwartz | |
| 2,115,482 A | 4/1938 | Crewe | |
| 3,308,825 A | 3/1967 | Cruse | |
| 3,374,856 A | 3/1968 | Wirt | |
| 3,556,097 A | 1/1971 | Wallace | 128/188 |
| 3,713,440 A | 1/1973 | Nicholes | 128/188 |
| 3,856,051 A | 12/1974 | Bain | 138/114 |
| 4,007,737 A | 2/1977 | Paluch | 128/188 |
| 4,068,664 A | 1/1978 | Sharp et al. | |
| 4,188,946 A | 2/1980 | Watson et al. | 128/204.22 |
| 4,230,114 A | 10/1980 | Feather | |
| 4,232,667 A | 11/1980 | Chalon et al. | 128/203.26 |
| 4,265,235 A * | 5/1981 | Fukunaga | 128/200.24 |
| 4,269,194 A | 5/1981 | Rayburn et al. | 128/719 |
| 4,282,869 A | 8/1981 | Zidulka | |
| 4,307,720 A | 12/1981 | Weber, Jr. | |
| 4,367,769 A | 1/1983 | Bain | 138/114 |
| 4,391,271 A | 7/1983 | Blanco | 128/203.12 |
| 4,407,280 A | 10/1983 | Trammell et al. | |
| 4,462,397 A | 7/1984 | Suzuki | 128/200.14 |
| 4,463,755 A | 8/1984 | Suzuki | 128/204.18 |
| 4,593,690 A | 6/1986 | Sheridan et al. | 128/207.15 |
| 4,596,246 A | 6/1986 | Lyall | 128/202.27 |
| 4,621,634 A | 11/1986 | Nowacki et al. | 128/204.18 |
| 4,637,384 A | 1/1987 | Schroeder | 128/204.18 |
| 4,718,568 A | 1/1988 | Palu | 220/86 |
| 4,809,706 A | 3/1989 | Watson et al. | 600/538 |
| 4,852,564 A * | 8/1989 | Sheridan et al. | 128/202.27 |
| 4,896,666 A | 1/1990 | Hinkle | 128/202.13 |
| 4,938,210 A | 7/1990 | Shene | 128/203.12 |
| 4,967,744 A | 11/1990 | Chua | 128/204.18 |
| 5,005,613 A | 4/1991 | Stanley et al. | 141/45 |
| 5,088,486 A | 2/1992 | Jinotti | 128/207.14 |
| 5,121,746 A | 6/1992 | Sikora | 128/203.12 |
| 5,140,983 A | 8/1992 | Jinotti | 128/207.14 |
| 5,181,916 A | 1/1993 | Reynolds et al. | |
| 5,195,527 A | 3/1993 | Hicks | 128/205.12 |
| 5,284,160 A | 2/1994 | Dryden | 128/203.12 |
| 5,320,093 A | 6/1994 | Raemer | 128/203.12 |
| 5,377,670 A | 1/1995 | Smith | 128/204.17 |
| 5,380,245 A | 1/1995 | Reiterman et al. | |
| 5,395,278 A | 3/1995 | Dickhut | |
| 5,404,873 A | 4/1995 | Leagre et al. | 128/204.18 |
| 5,427,570 A | 6/1995 | Chen | |
| 5,461,200 A | 10/1995 | Norcia | |
| 5,499,625 A | 3/1996 | Frass et al. | 128/207.15 |
| 5,546,930 A | 8/1996 | Wikefeldt | 128/201.13 |
| 5,548,093 A | 8/1996 | Sato et al. | |
| 5,597,385 A | 1/1997 | Moerke | |
| 5,623,922 A | 4/1997 | Smith | 128/204.18 |
| 5,632,734 A | 5/1997 | Galel et al. | 604/282 |
| 5,715,815 A | 2/1998 | Lorenzen et al. | 128/207.14 |
| 5,722,391 A | 3/1998 | Rosenkoetter et al. | 128/200.24 |
| 5,769,702 A | 6/1998 | Hanson | 454/63 |
| 5,778,872 A | 7/1998 | Fukunaga et al. | 128/202.27 |
| 5,819,733 A | 10/1998 | Bertram | 128/207.15 |
| 5,823,184 A | 10/1998 | Gross | 128/204.18 |
| 5,894,839 A * | 4/1999 | Rosenkoetter et al. | 128/200.24 |
| 5,983,891 A | 11/1999 | Fukunaga et al. | 128/200.24 |
| 5,983,894 A | 11/1999 | Fukunaga et al. | 128/205.29 |
| 5,983,896 A | 11/1999 | Fukunaga et al. | 128/202.27 |
| 6,003,511 A | 12/1999 | Fukunaga et al. | 128/202.27 |
| 6,223,777 B1 | 5/2001 | Smith et al. | 138/109 |
| 6,234,163 B1 | 5/2001 | Garrod | 126/80 |
| 6,536,428 B1 * | 3/2003 | Smith et al. | 128/203.17 |
| 6,564,799 B2 | 5/2003 | Fukunaga et al. | 128/205.29 |
| 6,672,338 B1 | 1/2004 | Esashi et al. | 138/119 |
| 6,874,500 B2 * | 4/2005 | Fukunaga et al. | 128/204.18 |
| 2003/0075176 A1 | 4/2003 | Fukunaga et al. | 128/203.12 |
| 2003/0183231 A1 | 10/2003 | Pedulla et al. | 128/204.18 |
| 2003/0188746 A1 * | 10/2003 | Daugherty | 128/203.12 |

FOREIGN PATENT DOCUMENTS

| | | |
|---|---|---|
| WO | WO 85/05277 | 12/1985 |
| WO | WO 91/19527 | 12/1991 |

OTHER PUBLICATIONS

Byrick, R.J., et al., "Rebreathing and Co-Axial Circuits: A Comparison of the Bain and Mera F", *Canad Anaesth Soc J*, vol. 28, pp. 321-328 (1981).

Dorsch, Jerry A., M.D., Dorsch, Susan E., M.D., *Understanding Anesthesia Equipment*, Chapter 7, The Circle Absorption System, pp. 201-202 and 220-221.

Forrest, P.R., "Defective Anaesthetic Breathing Circuit", *Canad J Anasth*, vol. 34, pp. 541-542 (1987).

Goresky, G.V., "Bain Circuit Delivery Tube Obstructions", *Canad J Anaesth*, vol. 37, p. 385 (1990).

Hannallah, R., et al., "A Hazard Connected With Re-Use of the Bains Circuit: A Case Report", *Canad Anaseth Soc J*, vol. 21, pp. 511-513 (1973).

Heath, P.J., et al., "Modified Occlusion Tests for the Bain Breathing System", *Anaesthesia*, vol. 46, pp. 213-216 (1991).

Jeretin, S. et al., "A Variable Deadspace Device for Use with the Engström Respirator", *Anesthesiology*, vol. 34, pp. 576-577 (1971).

Okazaki, et al., Effect of Carbon Dioxide (Hypocapnia and Hypercapnia) on Regional Myocardial Tissue Oxygen Tension to the Dog, *Anesthesiology*, vol. 71, No. 3A, A486 (1989).

Okazaki, et al., Effect of Carbon Dioxide (Hypocapnia and Hypercapnia) on Regional Myocardial Tissue Oxygen Tension in Dogs with Coronary Stenosis, *Anesthesiology*, vol. 73, No. 3A, A549 (1990).

Okazaki, et al., "Effect of Carbon Dioxide (Hypocapnia and Hypercapnia) on Internal Mammary-Coronary Arterial Bypass Graft Blood Flow and Regional Myocardial Oxygen Tension in the Dog", *Anesthesiology*, vol. 81, No. 3A, A717 (1994).

Paterson, J.G., et al., "A Hazard Associated with Improper Connection of the Bain Breathing Circuit", *Canad Anaesth Soc J*, vol. 22, pp. 373-377 (1975).

Pilbeam, Susan P., *Mechanical Ventilation*, 2nd Ed., Mosby year Book, St. Louis, Missouri, pp. 285-286 (1992).

Pontoppidan, H., et al., "Acute Repirator Failure in the Adult", *New England Journal of Medicine*, vol. 287, pp. 743-752 (1972).

Robinson, S., et al., "Safety Check for the CPRAM Circuit", *Anesthesiology*, vol. 59, pp. 488-489 (1983).

Scott, P.V., et al., "Variable Apparatus Deadspace", *Anaesthesia*, vol. 46, No. 9, pp. 1047-1049 (1991).

Shapiro, B.A., et al., "Clinical Application of Respiratory Care", *Yearbook Medical Publishers, Inc.*, pp. 351-352 ("Principles of Ventilator Maintenance")(1979).

Stoyka, W., "Usefulness of the Suwa Nomogram in Patients in Respiratory Fialure", *The Canadian Anaesthetists' Society Journal*, pp. 119-128 (1970).

Suwa, K., et al., "Change in $Pa_{CO_1}$ with mechanical dead space during artificial ventilation", *Journal of Applied Physiology*, vol. 24, pp. 556-561 (1968).

Advertisement of the CPRAM™ Coaxial Circuits by Dryden Corporation, Indianapolis, Indiana.

Advertisement of the ACE Breathing Circuit™ by the Meridian Medical Systems, Inc., Indianapolis, Indiana.

Fletcher, R., Scott, P.V., Jones, R.P., "The variable deadspace is not necessary," Correspondence reported in *Anaesthesia*, vol. 47, No. 7, pp. 623-624 (1992).

* cited by examiner

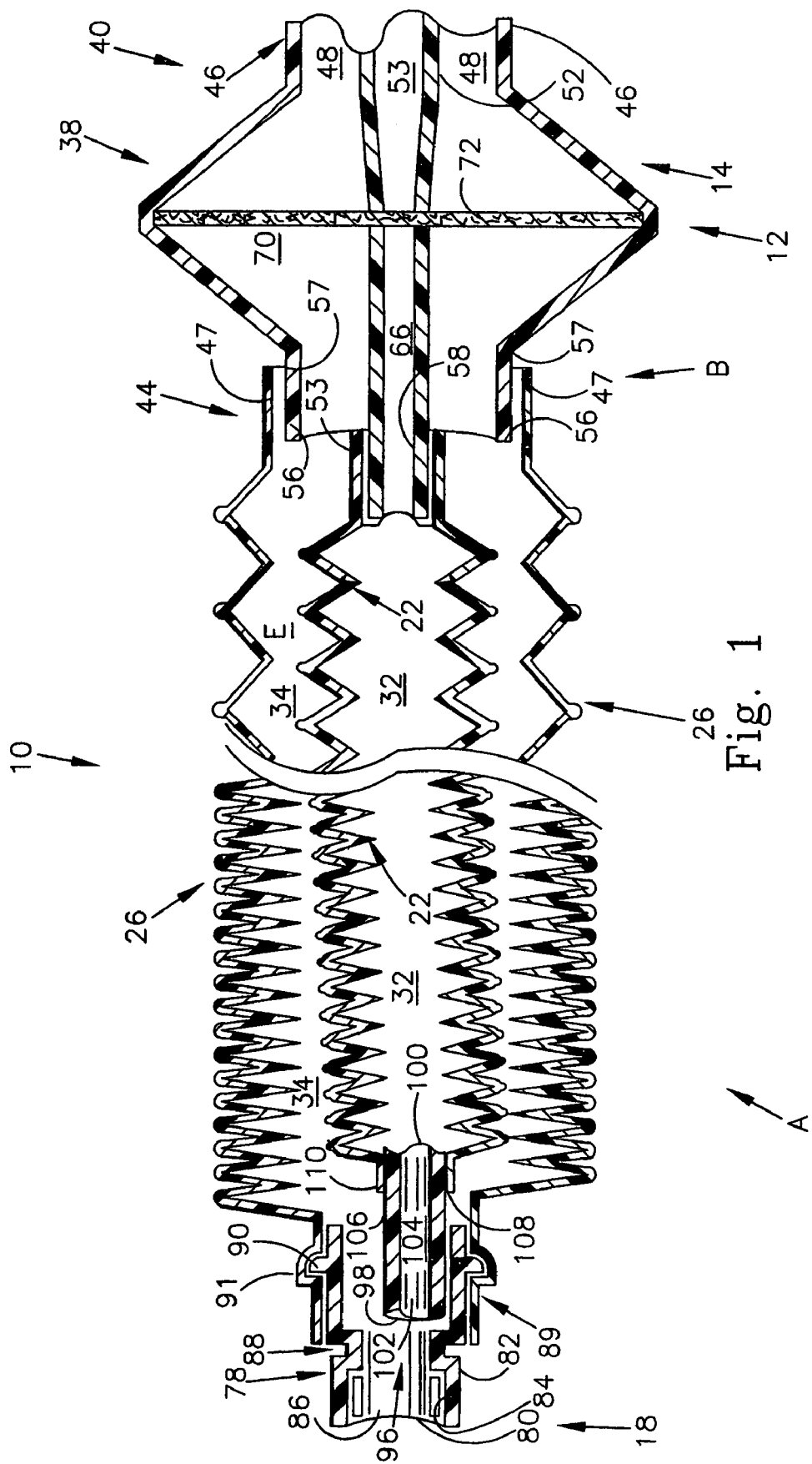

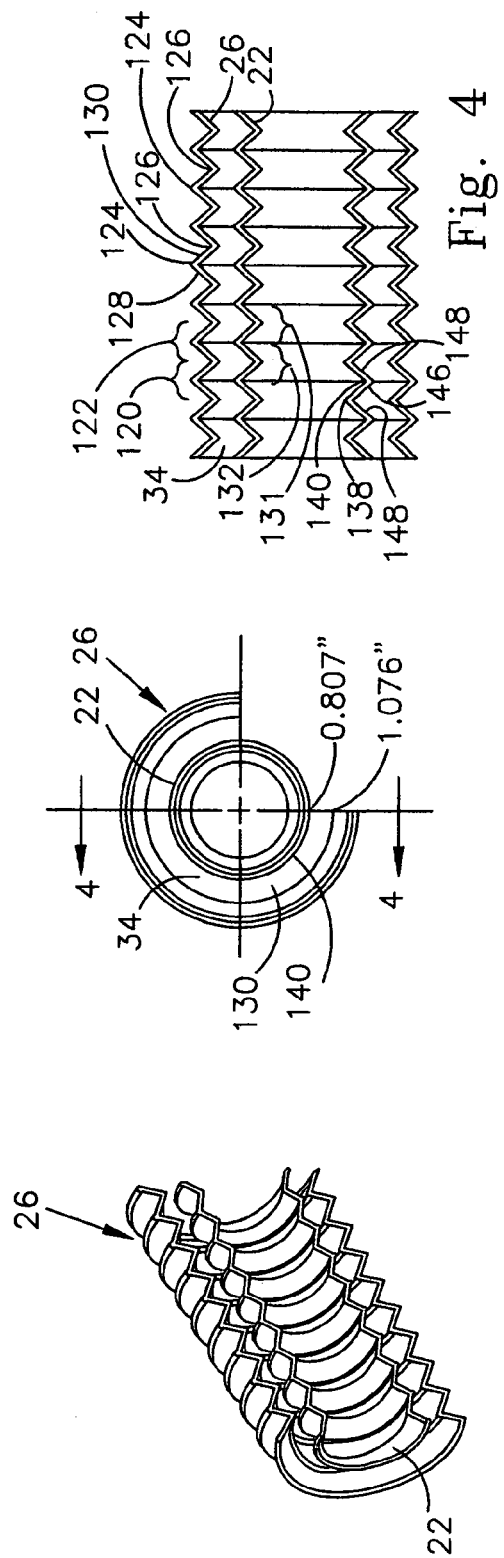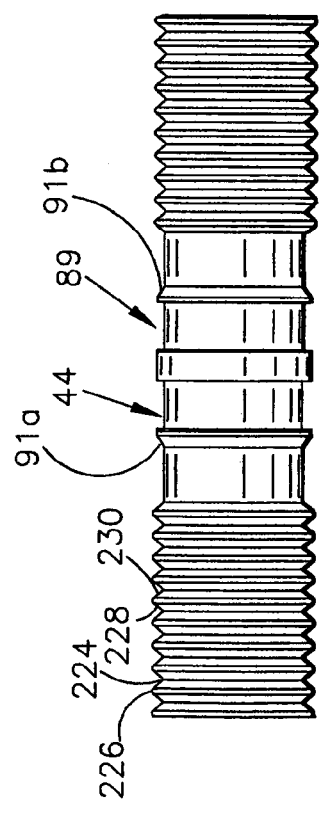

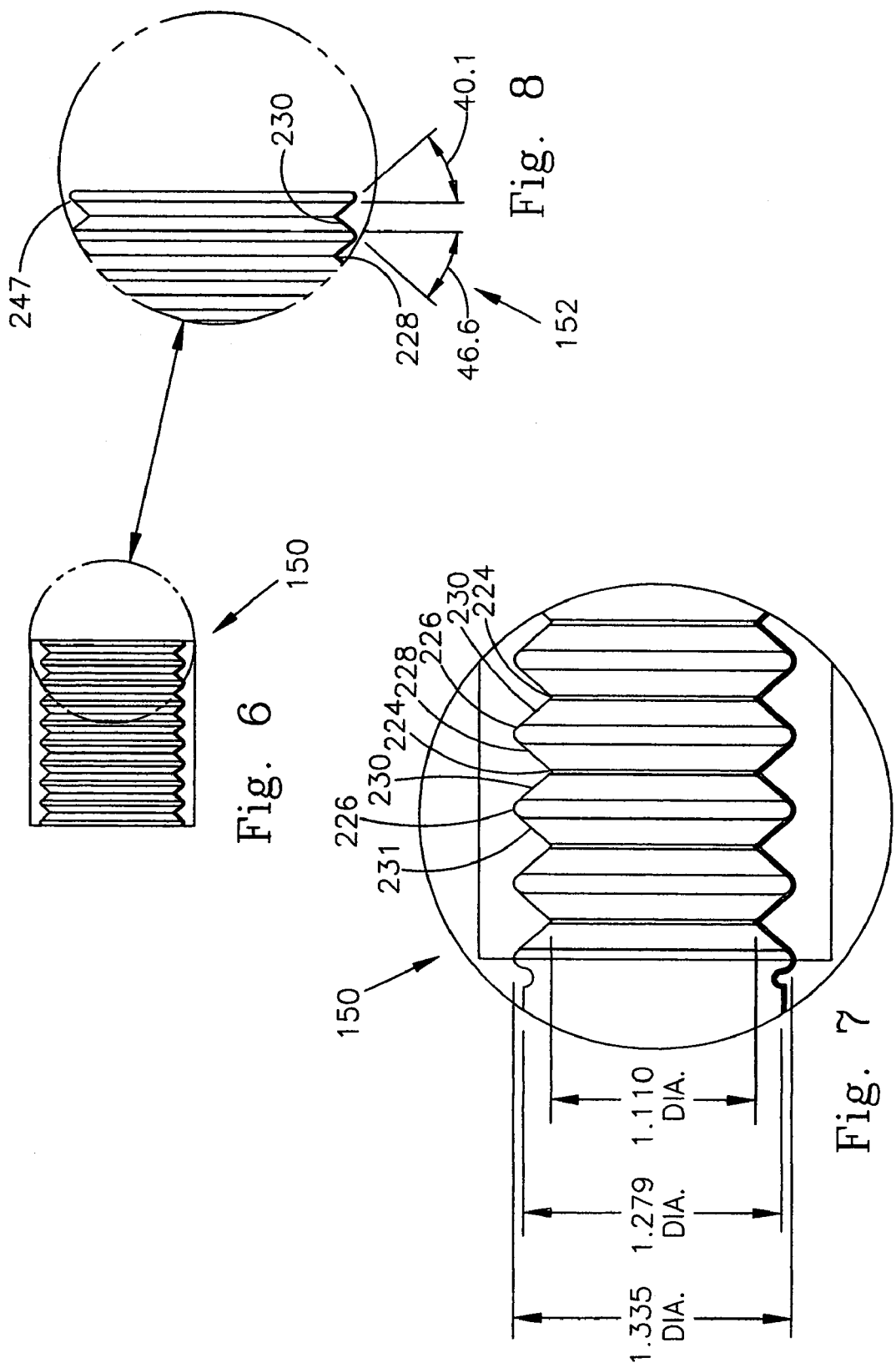

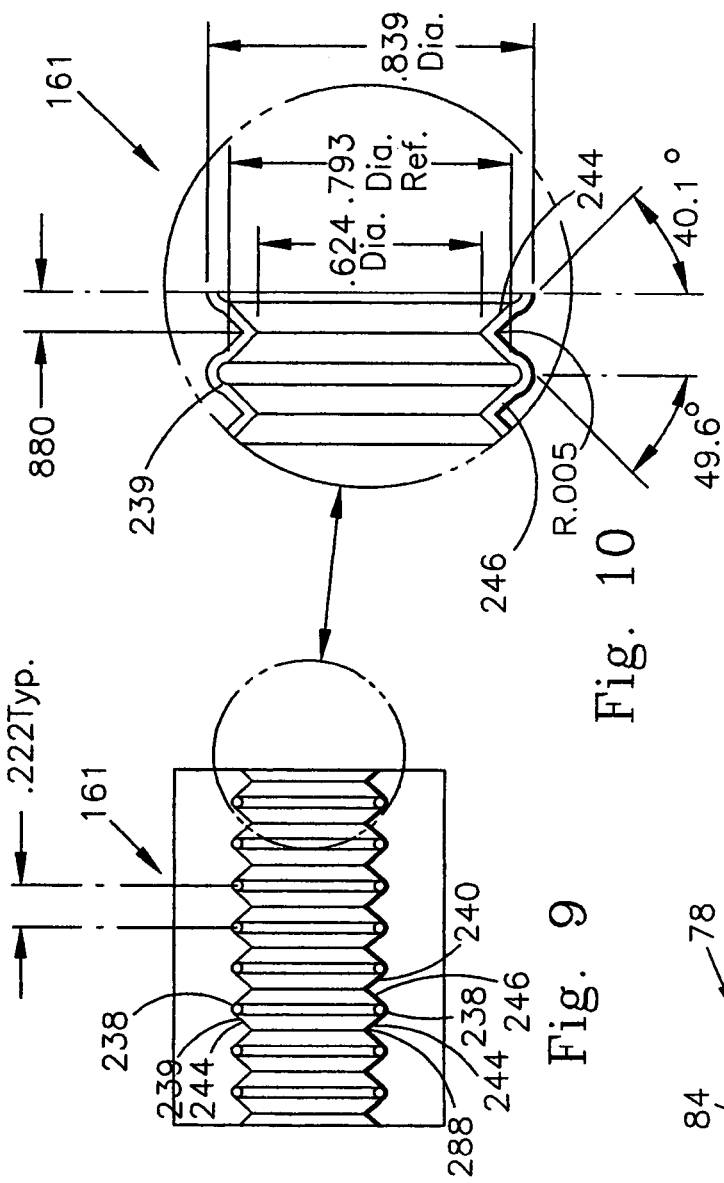
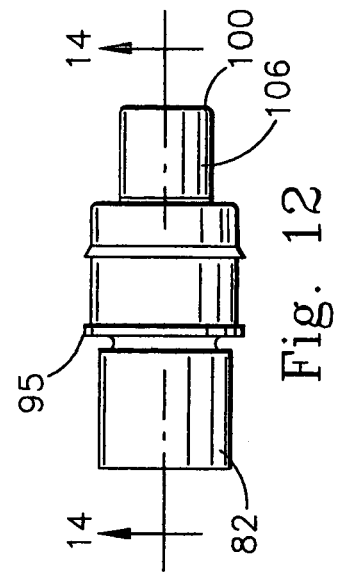
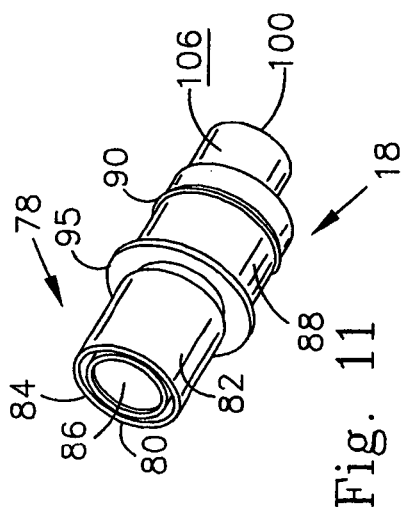
Fig. 9
Fig. 10
Fig. 11
Fig. 12

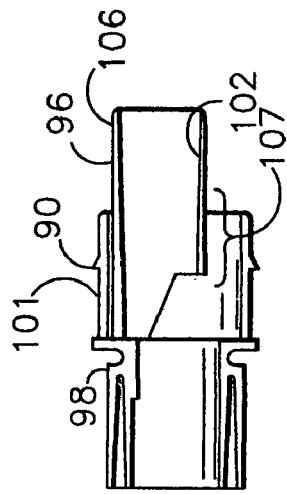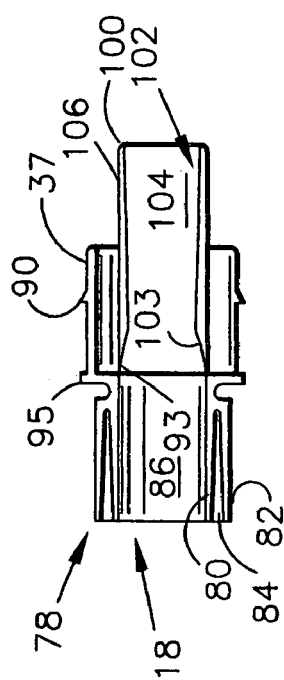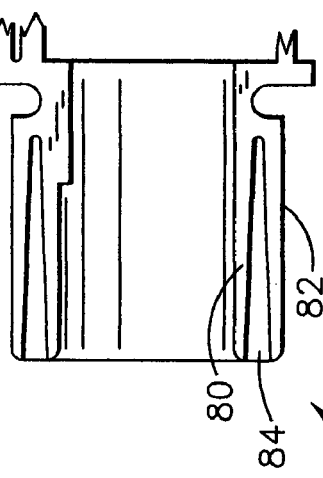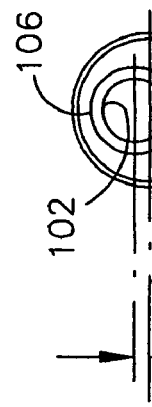

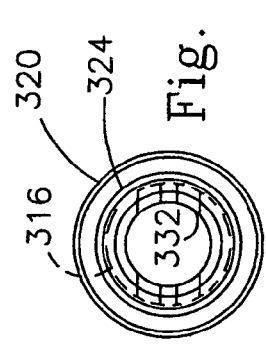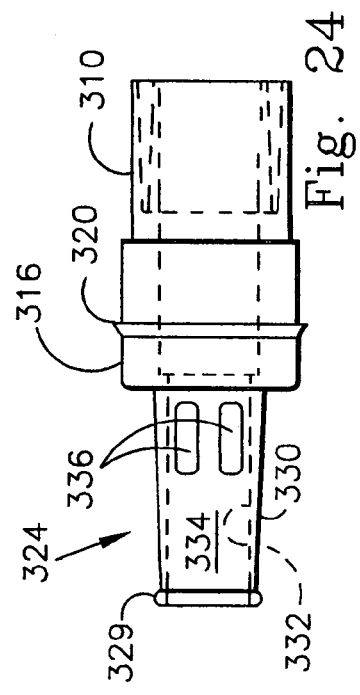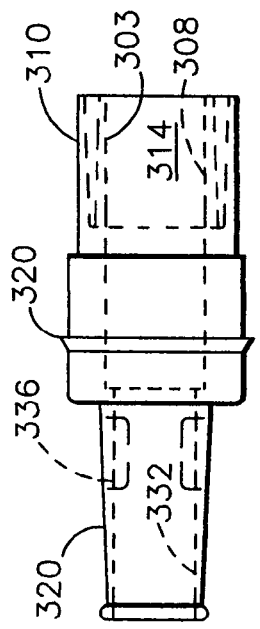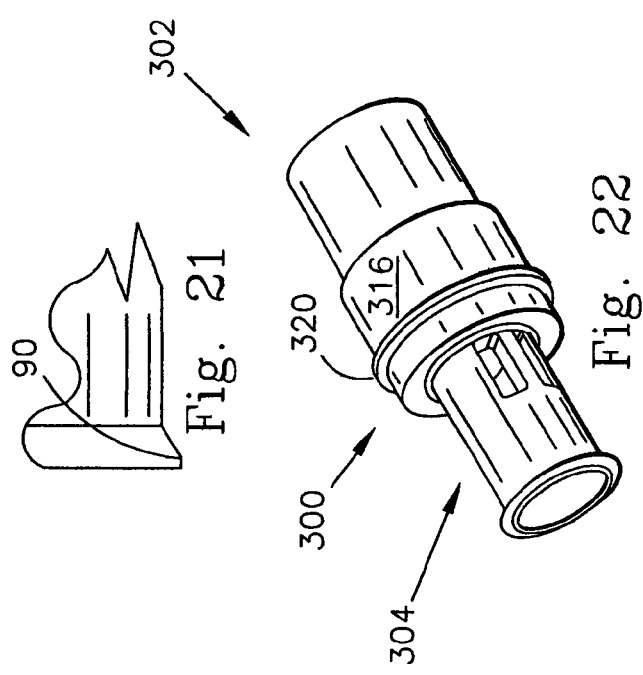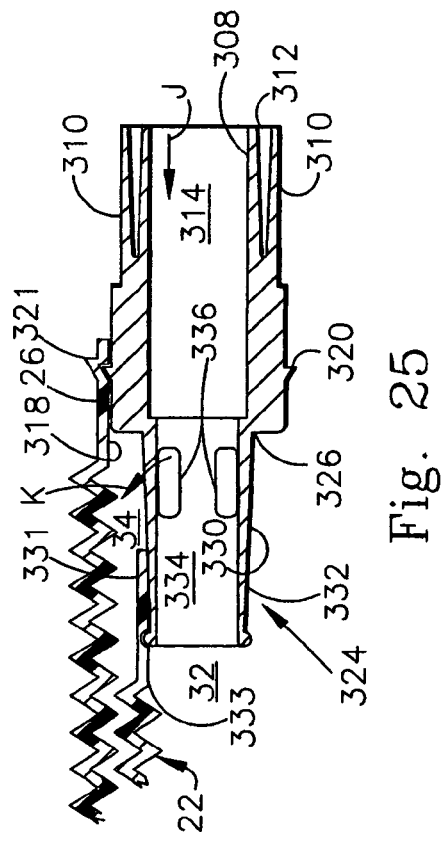

ADJUSTABLE LENGTH BREATHING CIRCUIT

I. PRIORITY CLAIM

This application claims the benefit of U.S. Provisional Patent No. 60/535,235, filed 9 Jan. 2004.

II. FIELD OF THE INVENTION

The present invention relates to a respiratory and anesthesia equipment, and more particularly to a breathing circuit for use in respiratory care or an anesthesia environment.

III. BACKGROUND OF INVENTION

To provide anesthesia to a patient during surgery, an anesthesia system is employed that includes a plurality of components. The primary component is an anesthesia machine, that regulates the flow of anesthesia gas and air to and from the patient. A carbon dioxide absorber may be attached to the anesthesia machine to remove carbon dioxide from the exhaled breath of the patient in a rebreathing circuit.

On the patient end, a face mask or an endo-tracheal tube is provided that can be coupled to the patient for delivering gas to the patient. Examples of face masks can be viewed at the assignee's web-site, www.KingSystems.com, or in Hinkle U.S. Pat. No. 4,896,666. Examples of tracheal tubes are shown in Frasse, U.S. Pat. No. 5,499,625; and Bertram, U.S. Pat. No. 5,819,733. These patient-coupled devices (the face mask and/or the endo-tracheal tube) are connected to the anesthesia machine in fluid (gaseous) communication via a breathing circuit that extends between the patient-coupled devices and anesthesia machine.

Several different types of breathing circuits exist. Two primary types of breathing circuits are dual limb circuits and unilimb circuits.

Dual limb circuits comprise a pair of separated tubes that include an inspiratory tube for delivering gas from the anesthesia machine to the patient, and an expiratory tube that delivers exhaled gas from the patient to the anesthesia machine. In a dual limb circuit, the two tubes comprise separate tubes that, at the patient end are typically fluidly coupled together by a "Y" or "T" tube. The machine ends of the tubes of a unilimb circuit are separate, with the machine end of the inspiratory tube being connected to the "outflow" port of the anesthesia machine, and the machine end of the expiratory tube being connected to the "inflow" port of the anesthesia machine. An example of a schematic representation of a dual-limb circuit can be seen in FIG. 1c of Fukunaga et al., Published U.S. Patent Application No. US2003/0183232A1 (2 Oct. 2003).

The second type of circuit is a unilimb circuit, wherein inspiratory tube are joined together. An example of a unilimb breathing circuit is shown in Leagre et al., U.S. Pat. No. 5,404,873; Fukunaga, U.S. Pat. No. 4,265,235 and Fukunaga et al, U.S. Pat. Nos. 5,778,872; 5,983,891; 5,983,894; 5,983,896; 6,003,511; 6,564,799; Fukunaga et al, Published U.S. Patent Applications Nos 2003/0075176 and US2003/0183231; and Sikora, U.S. Pat. No. 5,121,746.

As best shown in the Leagre '873 patent, a unilimb circuit typically includes a relatively rigid machine end (proximal) connector through which the circuit is coupled to an anesthesia machine; and a relatively rigid patient end (distal) connector that can be coupled to a face mask or tracheal tube, for coupling the breathing circuit to a patient. A relatively flexible expiratory tube extends between the patient end connector and the machine end connector. A relatively flexible, inspiratory tube is disposed co-axially with the expiratory tube. To promote better heat exchange to warm inspiratory gasses, the inspiratory tube typically has a smaller diameter than the relatively larger diameter expiratory tube so that the inspiratory tube can reside internally of the expiratory tube. The breathing circuit shown in the Leagre et al., '873 patent is sold commercially by the Assignee of the instant application, KING SYSTEMS CORPORATION, under the trademark of the UNIVERSAL F® breathing circuit.

Other breathing circuits sold by the Assignee of the present invention, KING SYSTEMS CORPORATION are shown, at least schematically, in the Fukunaga et al., '872; '894; 896; '511; and '799 patents discussed above.

The breathing circuits illustrated in the Fukunaga and Leagre patents are drawn as unilimb breathing circuits wherein the expiratory and inspiratory tubes are disposed co-axially with each other. Typically, the inner, relatively smaller diameter tube is used as an inspiratory tube, and the outer, relatively larger diameter tube is employed as the expiratory tube. A noteworthy difference between the breathing circuit shown in the Leagre patent and those shown in the Fukunaga patents resides in the differences in the machine end couplers of the circuits.

The inspiratory and expiratory tube of the Leagre and Fukunaga devices, as embodied in the UNIVERSAL F® and UNIVERSAL F2® are similar, as both employ a corrugated inspiratory tube and a corrugated expiratory tube. The corrugated inspiratory tubes and corrugated expiratory tubes are corrugated to have a single rest length, while permitting the length of the tube to be expanded, or contracted.

The variability of the length of the corrugated inspiratory and expiratory tubes is engineered into the UNIVERSAL F® and UNIVERSAL F1® circuits, to permit the length of the tubes to be stretched (lengthened) and compressed (shortened) for short periods of time. This variation in length often occurs when the relative position of the patient and the anesthesia machine is changed, and usually involves the need to stretch the tube during this change in relative position. However, as the expiratory and inspiratory tubes are designed to have a fixed rest length, any change in the length of the inspiratory and expiratory tubes from their fixed rest length exerts "stress" on the expiratory tubes, and causes the expiratory tube to exert either a compressive or an expansive force, (as appropriate) to enable the tube to return back to its unitary rest length.

During the stretching of the expiratory tube, the inspiratory tube typically does not stretch as it is only connected to the machine end connector in the UNIVERSAL F® and UNIVERSAL F2® breathing circuits. However, both the inspiratory and expiratory tubes are likely to stretch in breathing circuits such as one sold by Meridian Medical Systems, as the Meridian Medical breathing circuit employs an the inspiratory tube that is connected to both the machine end and patient end connectors.

Another reason for employing single rest length corrugated tubes is to prevent the tubes from becoming kinked. It is highly desirable to prevent such kinking, because such kinking can result in the obstruction or blockage of flow of gas in the tube, in much the same way that the flow of water is obstructed or blocked through a garden hose when it becomes kinked.

Another unilimb breathing circuit is shown in Sikora, U.S. Pat. No. 5,121,746. The Sikora device employs a unilimb circuit, wherein an expiratory and inspiratory tube are joined at a common wall, to give the breathing circuit a θ like configuration. The tubing shown in the Sikora patent also appears to be corrugated, no doubt, for many of the same reasons as a corrugated tube is employed in the UNIVERSAL F® and UNIVERSAL F2® devices described above.

Although the devices described above, and in particular the UNIVERSAL F® and UNIVERSAL F2® devices perform their intended functions quite admirably, room for improvements exists.

One source of difficulties resides in the unitary rest length of the breathing circuit the unitary rest length requires multiple lengths of tubing to be manufactured, to accommodate different situations and preferences. Some medical professionals prefer relatively shorter (e.g. 44 inch, 112 cm) length tubes, whereas other medical professionals prefer to move the anesthesia machine further away from the patient so that it is less obtrusive, thereby requiring relatively longer (e.g. 88 inch, 224 cm) breathing circuits.

From a manufacturer's standpoint, this desire for different circuit lengths requires the manufacturer to manufacture breathing circuits in a variety of lengths. From the viewpoint of a user (e.g. hospital or surgical center), these different desired lengths require the end user to inventory several different circuit lengths.

Another difficulty is encountered in shipping. Because unitary rest length circuits using corrugated tubing have a single rest length, the tube must normally be sized to have a relatively long (e.g. 44 or 88 inches; 112 or 224 cm) rest length, so that when the device is in use, it is long enough to serve its purpose while being neither stretched nor compressed. Because of the elasticity of the single rest length corrugated tube, the tubing when stretched exerts a compressive force, that tends to compressively shorten the tube back to its rest length.

It is not recommended that the device be used when stretched, as the compressive force exerted by the tube can help facilitate both external disconnects, wherein the breathing circuit is pulled away from its coupling to either the machine or the patient; or internal disconnects wherein the corrugated breathing tubing is pulled away from one of the machine or patient end couplings. It is desirable to avoid both internal and external disconnect inducing situations.

As a result of this, a 44 inch (112 cm) breathing circuit, for example, has a 44 inch (112 cm) rest length that ordinarily cannot be compressed (and thereby made smaller for shipping) for any significant length of time without the exertion of an external clamping force. The inability to change the rest length to shorten it, without the imposition of external clamping forces, requires the manufacturer to provide enough storage space in a container or box, to accommodate the entire 44 inch (112 cm) length of the hypothetical 44 inch (112 cm) breathing tube. Additionally, it requires the hospital or surgical center user to provide storage space sufficient to accommodate the entire 44 inch (112 cm) length of the breathing circuit.

From the foregoing discussion, it will be appreciated that it would be desirable to have a breathing circuit, that could be compressed, to take up less space during shipment. Additionally, it would be desirable to construct a breathing circuit including a plurality of sustainable rest lengths, so that, for example, a single device could be extended from its fully compressed (shipment) length, to, for example, a partially extended "short tube length" having an overall length of about 44 inches (112 cm), and stretched further into a fully extended (fully decompressed) position wherein it would have a rest length equal to that of a longer breathing circuit, such as an 88 inch (224 cm) breathing circuit.

One object of the present invention is to provide such a breathing circuit having a plurality of fixed rest lengths, so that the device can be placed in a fully compressed position, to reduce the length for shipping, storage and some anesthesia applications, but also be extended, and sustainably be maintained in a plurality of extended rest length positions, to provide a desired greater length than the compressed position. Preferably, the device is also sustainable in a variety of rest lengths that vary in length between the fully compressed position and the fully extended position of the breathing circuit.

IV. SUMMARY OF THE INVENTION

In accordance with the present invention, a unilimb breathing circuit is disclosed having a proximal end coupling member, a distal end coupling member, an expiratory tube extending between the proximal and distal end coupling members, and an inspiratory tube extending between the proximal and distal end coupling members. The expiratory tube comprises a pleated expiratory tube that is expandable between a fully compressed rest position, and a fully expanded rest position, and has a plurality of intermediate rest positions. At the plurality of intermediate rest positions, the expiratory tube is capable of maintaining its rest length without the exertion of an external force. The inspiratory tube comprises a pleated inspiratory tube having a length that is variable between a fully compressed rest position and a frilly expanded rest position, and includes a plurality of intermediate rest positions between the fully expanded rest position and the fully compressed rest position. The inspiratory tube, like the expiratory tube is capable of maintaining these intermediate rest positions, without the exertion of an external force.

Preferably, the length of the inspiratory tube is greater than the length of the expiratory tube by between about 1 and 7 inches, and optimally by about 4 inches when each are fully extended.

In one preferred embodiment, the expiratory tube and inspiratory tube are disposed generally co-axially to each other, and the distal end coupling includes an expiratory tube coupling member that is radially offset from being centered and coaxial near the patient end connector.

In another preferred embodiment of the present invention, the inspiratory tube has an inner diameter and an outer diameter, and the expiratory tube has an inner diameter and an outer diameter. The outer diameter of the inspiratory tube and the inner diameter of the expiratory tube are sized relative to each other so that the outer surface of the inspiratory tube and the inner surface of the expiratory tube define an expiratory passageway wherein the resistance of airflow along the expiratory passageway is minimized. Additionally, the differences in the sizes between the inner diameter of the expiratory tube and the outer diameter of the inspiratory tube should be sufficiently small enough as to facilitate the generally linear compression the inspiratory tube when the expiratory tube is linearly compressed.

One feature of the present invention is that corrugated tubing of an accordion type is employed wherein each pleat is capable of being positioned in a maintainable expanded rest position and a maintainable compressed rest position. As a breathing tube is comprised of a large number of such pleats, the tube is capable of having a large number of rest lengths. This feature has the advantage of enabling the user to vary the working length of the tube to suit his/her particular needs. Additionally, it enables the tube to be compressed during shipment and storage to reduce the amount of space required by the tube during shipping and storage, but permits the tube to be expanded during usage, to extend to a length that accommodates the operating room personnel, and in particular, the anesthesiologist.

Another feature of the present invention is that the outer diameter of the expiratory tube and the inner diameter of the inspiratory tube are sized so as to minimize resistance of airflow through the expiratory gas passageway that exists between the outer surface of the inspiratory tube and the interior surface of the expiratory tube.

During surgery, it is important to keep the gas passageways, such as the inspiratory passageway and expiratory passageway as unobstructed as possible, to promote the free flow of gas therethrough. As a general rule, it is desirable to minimize the resistance of airflow that is caused by tubing members. In this regard, it would be contraindicated to use, for example, a tube having a series of radially extending baffles (such as would be found in a car muffler), as such baffles would increase the resistance of flow through the passageway.

In a normal, unilimb breathing circuit, such as the UNIVERSAL F® and UNIVERSAL F2® devices described above, resistance is minimized by appropriately selecting an inspiratory tube having an outer diameter size, and an expiratory tube having an inner diameter size that provides a sufficient space between the outer surface of the inspiratory tube and the inner surface of the expiratory tube to allow gas to flow therethrough unimpeded. As the UNIVERSAL F® and UNIVERSAL F2® devices both employ unitary rest stop-type tubing, the tube engineer needs to be concerned about air resistance between the inspiratory tube and expiratory tube within the expiratory gas flow path at essentially a single relative length of the inspiratory and the expiratory tubes.

With the present invention, sizing the diameters of the expiratory tube and the inspiratory tubes becomes a significantly more difficult task. One reason that sizing is more difficult is that the outer and inner diameters of each tube will vary depending upon whether the corrugations are their compressed or extended position. It has been found generally, that the inner diameter of the expiratory tube is smaller when the expiratory tube's pleats are compressed, than when the corrugations are expanded. Similarly, the outer diameter of the inspiratory tube is greater when the inspiratory tube is compressed, as compared to when its pleats are expanded.

At first blush, it might appear that a simple solution existed to this sizing problem by maximizing the difference between the outer diameter of the inspiratory tube and the inner diameter of the expiratory tube, such as might occur by greatly enlarging the diameter of the expiratory tube, and/or greatly reducing the diameter of the inspiratory tube. However, this course of action does not necessarily result in a well functioning breathing circuit. Although this course of action would help to reduce resistance, it has the drawback of adversely affecting the ability of the user to adjust the length of the breathing circuit, and in particular, to vary the length of the inspiratory tube.

If the difference between the outer diameter of the inspiratory tube and the inner diameter of the expiratory tube is too great, the inspiratory tube will have a greater propensity to become kinked, or become difficult to compress when the length of the tube is shortened. As discussed above, kinking of the tube is highly undesirable. Additionally, resistance can be impaired, because compression of the inspiratory tube in an overly large expiratory tube interior can cause the inspiratory tube to lose its linearity during compression, and thereby become "snake-like". It has been found by the Applicant's that an undulating, wave-like configuration of the inspiratory tube, within the expiratory tube may help to increase resistance. Additionally, resistance within the inspiratory gas passageway can also increase as the inspiratory tube deviates from a generally linear path, to more curved, undulating path.

It is also a feature of the present invention that, while the inspiratory tube and expiratory tube are disposed generally co-axially to each other, the patient end coupling of the inspiratory tube couples the inspiratory tube at a position that is offset radially, relative to the axis of the expiratory tube. This offset arrangement provides a better defined, less resistance prone passageway for the expiratory gas to flow from the patient, and into the expiratory pathway between the expiratory tube and the inspiratory tube. In practice, the gas flowing between the patient end coupling and the expiratory tube is flowing in a direction generally from the patient end coupling into the expiratory tube.

Another feature of the present invention is that inspiratory and expiratory flexible tubes are designed so that the corrugations of the tube can be repeatedly moved between their compressed position and their expanded position, without the corrugations losing their ability to hold designated rest lengths. This feature has the advantage of enabling the tube to be sized and resized, either at the beginning of a procedure, so that the user can obtain the desired length, or during a procedure, if a user decides to change the effective length of the breathing circuit in mid-procedure. These repeated changes in the effective length of the breathing circuit can be made without fear that the breathing tube cannot later be set at any one of its desired effective rest lengths.

These and other features of the present invention will become apparent upon review of the drawings and detailed description below, that sets forth the best mode of practicing the invention, as perceived presently.

V. BRIEF DESCRIPTION OF DRAWINGS

FIG. 1 is a sectional, side view of the present invention, showing a portion of the breathing circuit of the present invention in its expanded mode, and another portion of the invention in its compressed mode;

FIG. 2 is a sectional perspective view of a segment of the inspiratory and expiratory tubes of the present invention;

FIG. 3 is an end view of the inspiratory and expiratory tubes of the present invention, with the end coupling removed;

FIG. 4 is a sectional view taken generally along lines 4—4 of FIG. 3;

FIG. 5 is a plan view of two coupled expiratory tubes of the present invention, for illustrating the manner in which they are manufactured;

FIG. 6 is a plan view of the expiratory tube engaging surface of a mold block used to construct the expiratory tube of the present invention;

FIG. 7 is a greatly enlarged, partial view of the expiratory tube engaging surface of the mold block of FIG. 6;

FIG. 8 is an expanded (relative to FIG. 6) view of the expiratory tube engaging surface of the mold block used to manufacture the expiratory tube of the expiratory tube of the present invention;

FIG. 9 is a plan view of a mold block employed in the manufacture of the inspiratory tube of the present invention, showing the inspiratory tube engaging surface of the block;

FIG. 10 is a greatly enlarged view of a portion of the inspiratory tube engaging surface of the mold block used to make the inspiratory tube of the present invention;

FIG. 11 is a perspective view of a patient end connector of the breathing circuit of the present invention;

FIG. 12 is a top view of the patient end connector of the present invention;

FIG. 13 is a side view of the patient end connector of the present invention, showing the interior surfaces in phantom;

FIG. 14 is a sectional view taken generally along lines 14—14 of FIG. 12;

FIG. 15 is a sectional view taken generally along lines 15—15 of FIG. 13;

FIG. 16 is a sectional view taken generally along lines 16—16 of FIG. 13;

FIG. 17 is a greatly enlarged, partly broken away view of the mask/tracheal tube coupler of the patient end connector of the present invention;

FIG. 18 is a patient end view of the patient end connector of the present invention;

FIG. 20 is an end view of the patient end connector of the present invention, generally showing a view as taken from the tube-receiving end of the patient end connector;

FIG. 21 is a diagrammatic view, showing the dimensioning of the expiratory tube gripping spike of the patient end connector;

FIG. 22 is a perspective view of an alternate embodiment patient end connector of the present invention;

FIG. 23 is an end view of the patient end connector of the present invention, as shown from the tube-receiving portion of the patient end connector shown in FIG. 22;

FIG. 24 is a top view of the alternate embodiment patent end connector, showing the interior surfaces in phantom;

FIG. 25 is a sectional view taken generally along lines a—a of FIG. 24;

FIG. 26 is a plan view, showing the alternate embodiment patient end connector of FIG. 22 in a position similar to that shown in FIG. 25, with interior surfaces shown in phantom;

VI. DETAILED DESCRIPTION

Figure 19:
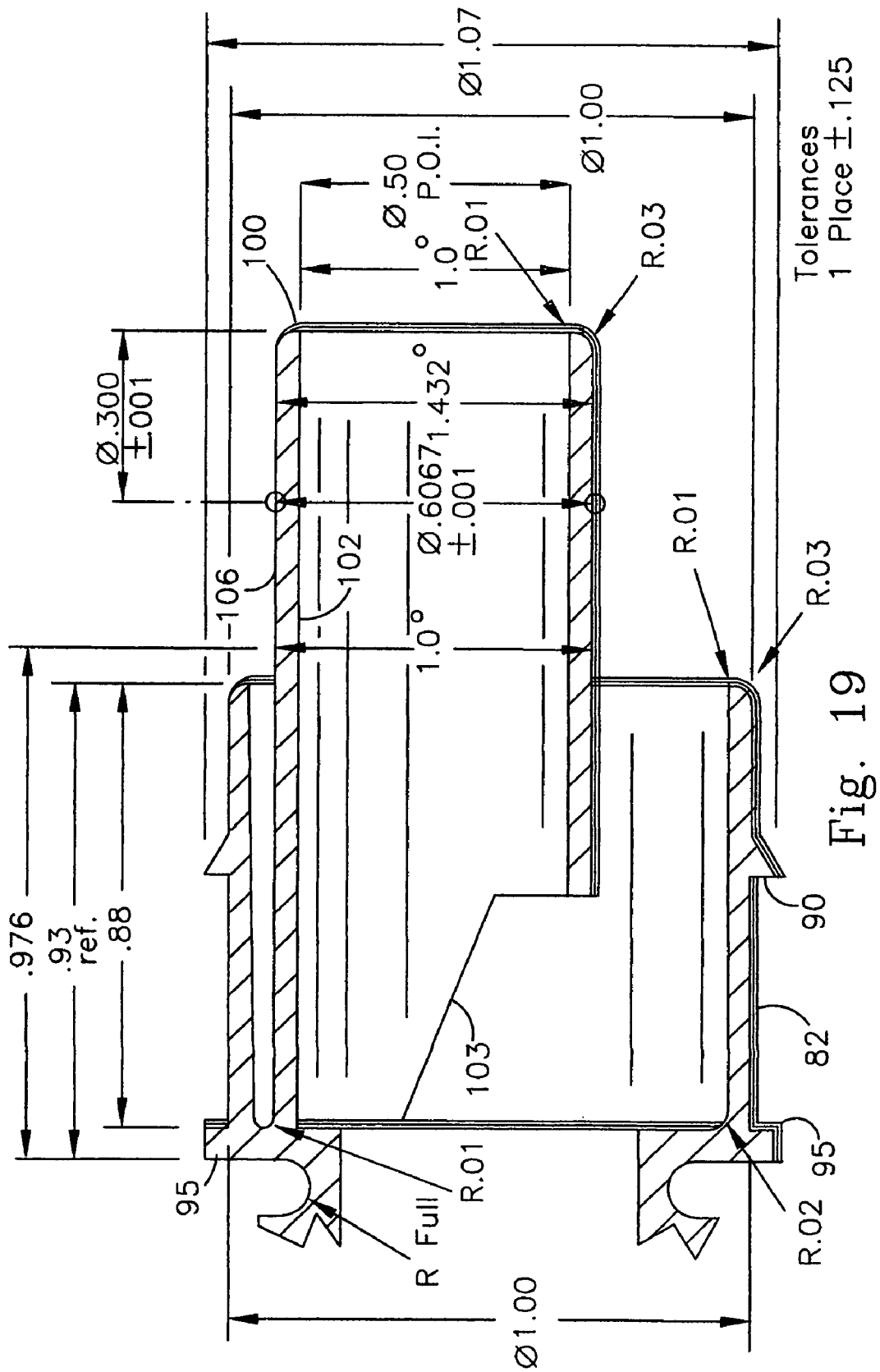
FIG. 19 is a greatly enlarged, sectional view of the inspiratory and expiratory tube receiving portion of the patient end connector of the present invention.

Breathing circuit 10 of the present invention is best shown in the figures. Turning now to FIG. 1, the breathing circuit 10 includes a machine end connector 12, that is disposed at the proximal end of the breathing circuit 10, and in the embodiment shown in FIG. 1 serves the dual purpose of being both a machine end connector 12, and a filter 14. Although the machine end connector 12 is shown as including filter 14, the machine end connector 12 can also be designed to comprise a filter-less type machine end connector 12.

A patient end connector 18 is disposed at the distal, or patient end of the circuit 10. A flexible, corrugated inspiratory tube having a plurality of sustainable rest lengths extends between the patient end connector 18 and the machine end connector 12, and is provided for carrying inspiratory gas, in a direction from the machine end connector 12 toward the patient end connector 18, as indicated generally by arrow I. A flexible corrugated sustainable multi-rest length expiratory tube 26 also extends between the patient end connector 18 and the machine end connector 12, and is provided for carrying expiratory gas away from the patient, from the patient end connector 18, toward the machine end connector 12, in a direction indicated generally by arrow E.

Both the inspiratory tube 22 and the expiratory tube 26 are fixedly coupled, at their machine ends to the machine end connector 12. Similarly, both the inspiratory tube 22 and the expiratory tube 26 are fixedly coupled, at their patient end, to the patient end connector 18.

As will be discussed in more detail below, the inspiratory tube 22 and expiratory tube 26 are corrugated, with corrugations that are each designed to assume both an expanded position, as shown on the right side of the drawing of FIG. 1 as indicated by arrow B, and a compressed position, as shown on the left side of the drawing, indicated by arrow A. Unlike prior art devices, the inspiratory tube 22 and expiratory tube 26 are capable of assuming rest positions wherein one or more of the corrugations reside in either their compressed position or their expanded position. This ability of the corrugations to assume a rest position in their compressed positions and in the expanded positions permits the length of the breathing circuit to be fixed at any one of a large plurality of different rest lengths. These rest lengths can be maintained without the exertion of an external force on the tube.

As discussed above, this feature differs from those devices wherein a single rest length tube was employed. Single rest length tubing is unable to maintain either an expanded or compressed position (relative to the rest length) without the exertion of some outside force, such as a clamp or the like, since the elasticity and spring property of the single rest length corrugated tubing in the prior art exerts a stress on the tubes, to move the tubes from their compressed or expanded states back toward their rest positions.

The machine end connector/filter 14 includes a casing 38 that defines an interior. The casing 38 includes a machine engaging end 40 to which can be attached a proximal terminal, as described in the Fukunaga's '872 patent discussed above, that connects to an anesthesia machine. Alternately, the machine engaging end 40 can be connected directly to the anesthesia machine if the anesthesia machine (not shown) contains an appropriately sized coupling and port for receiving the machine engaging end 40.

It should also be noted that the machine engaging end can include a variety of other configurations, such as the configuration shown in Leagre, U.S. Pat. No. 6,129,082 or Leagre and Burrow, U.S. Pat. No. 5,404,873.

The machine engaging end 40 includes a first, generally cylindrical expiratory port connector 46 for defining an expiratory port 48, through which expiratory gasses can pass from the expiratory port 48 into the anesthesia machine. A first inspiratory port connector 52 is generally cylindrical, and coaxial with the first (proximal) end 47 of the expiratory tube 26. The first inspiratory port is provided for being coupled to the outflow port of an anesthesia machine, and defines an interiorly disposed inspiratory port 53 through which gas, and rebreathed air can pass from the anesthesia machine into the inspiratory port.

A first expiratory tube connector is disposed at the tube engaging end 44 of the machine end connector/filter 14, and includes a radially outwardly facing, axially extending cylindrical surface 57 for receiving the first (proximal) end 47 of the expiratory tube 26. The radially inwardly facing, axially extending interior surface of the proximal end 47 of the expiratory tube 26 is fixedly coupled and engaged to the radially outwardly facing surface 57 of the first expiratory tube connector 56. Preferably, the connection between the first end 47 of the expiratory tube 26 and the radially outwardly facing surface 57 is designed to be snug and permanent to prevent a disconnect between the two. This snug, secure fixed coupling can be achieved either chemically, through the use of glue, sizing to create a snug fit, or by some mechanical attachment means such as a band or other attachment protocol, such as sonic welding.

The tube engaging end 44 of the machine end connector/filter 14 also includes a first inspiratory tube connector 58, that is sized for receiving, on its generally cylindrical, radially outwardly facing surface, the radially inwardly facing cylindrical surface of the first (proximal) end 53 of the inspiratory tube 22. The ends 53, 47 of the inspiratory tube and expiratory tubes are sized and configured for receiving the connectors 58, 56 and are often referred to as the "cuffs" of the tubes 53, 47.

Similar to the connection between the expiratory tube 26 and the first expiratory tube connector 56, the connection between the first inspiratory tube connector 58 and the first end 53 of the inspiratory tube 22 should be a snug, permanently fixed fit that is designed to maintain the first end 53 of the inspiratory tube 52 on the connector 58, to prevent a disconnect therebetween. The connection between the cuffs of the inspiratory tube 22 and the machine end 14 and patient end 18 connectors is more critical generally, and as such, should be designed to be as strong as, if not stronger than the coupling between the cuffs of the expiratory tube and the machine end connector 12 and patient end connector 18.

It will be noted that the inspiratory tube connector 58 extends generally outwardly past the end of the inspiratory tube connector 58. This additional length is provided to facilitate the manufacturing process, to make it easier to attach the first end 53 to the inspiratory tube 22 to the first end inspiratory tube connector 58.

It is important within the casing 38 to maintain the expiratory flow path 70 separate from the inspiratory flow path 66; as it is generally undesirable to mix the inspiratory and expiratory gasses at the machine end of the circuit 10. To this end, the casing 38 is shown to maintain the inspiratory flow path 66 separate and distinct from the expiratory flow path 70.

An example of a filter casing that will accomplish this function is a filter such as that shown in the Fukunaga '894 patent, along with the UNIVERSAL F2® Co-Axial Filter sold by King Systems Corporation, and described at www.KingSystems.com.

The filter media 72 is disposed within the interior of the casing 38. The filter media 72 is designed so that all of the expiratory gas and all of the inspiratory gas that passes through the filter 14 must pass through the filter media 72. The filter media 72, is designed to trap pathogens and other germs, to prevent these pathogens and germs from passing through the filter media 72, and either contaminating the anesthesia machine with patient-origin pathogens and germs; or alternately, contaminating the patient with anesthesia machine origin pathogens and germs.

The patient end connector 18 includes a patient device receiving connector 78 that is designed for receiving a patient device, such as a face mask (not shown), or a tracheal tube, such as an endo-tracheal tube (not shown). Examples of face masks and tracheal tubes can be viewed at www.KingSystems.com The patient device receiving connector 78 includes an interior cylindrical connector member 80, and an exterior cylindrical connector member 82, that are spatially separated by a small distance, to form a cylindrical slot 84. This configuration is designed to receive the various types of patient connector devices. The size and shape of the patient device receiving connector 78 is largely dictated by ISO standards that have been implemented to both help to ensure patient safety, and to foster standardization.

The patient device receiving connector 78 defines an interiorly disposed gas receiving port 86, through which both expiratory and inspiratory gas can pass between the breathing circuit 10 and the patient device. The patient end connector 18 also includes a second (distal) end expiratory tube receiving connector 90, that is generally cylindrical in configuration, and is sized and shaped for receiving the second end (cuff) 89 of the expiratory tube 26. Although the expiratory tube receiving connector 88 is generally cylindrical in configuration, it does include a raised, radially outwardly extending circumferential spike 90, that is designed for receiving a complementarily formed circumferential spike receiving ring 91, that is formed in the second end cuff 89 of the expiratory tube. The spike 90 and the receiving ring 91 are complementarily configured, so that the spike 90 engages the receiving ring 91, to help lock on and secure the second end 89 of the expiratory tube onto the expiratory tube receiving connector 88.

The patient end connector is best described in connection with FIGS. 1 and 11–19. Turning now to FIGS. 17 and 18, two views of the patient device receiving connector 78 of the patient end connector 18 are shown, that provide dimensions of the various parts, spaces and gaps of the patient connector of an exemplary embodiment of the patient device receiving portion 78 of the patient end connector.

As best shown in FIG. 11, a radially outwardly extending, circumferential stop ring is provided that extends radially outwardly above the surface of the expiratory tube receiving connector 88. The stop ring 95 serves to prevent unwanted axial movement of the expiratory connector on the expiratory receiving connector 88.

The tube receiving portion of the patient end connector 18 also includes an inspiratory tube receiving connector 96 that generally comprises a cylindrical tube having a distal end 98, and a proximal end 100. The inspiratory receiving member 96 is generally tubularly, cylindrically shaped and includes a radially inwardly facing surface 102 that, at its distal end 98 terminates in the angled, cut-out portion 103, to better foster the flow of inspiratory gas out of the hollow interior passageway 104 of the inspiratory tube receiving connector 98.

As best shown in FIGS. 13 and 14, the distal end of the inspiratory tube receiving connector 96 is formed as a part of, and is coupled to a axially outwardly facing, radially extending wall member 101. This unitary construction/connection fixedly couples the inspiratory tube receiving connector 96 to the remainder of the patient end connector 18.

It should be noted, from the dimensions given in FIG. 14, that the inspiratory tube receiving connector 98 is radially offset from the center of the connector 18. As shown in FIG. 14, the center of the inspiratory tube receiving connector 96 is preferably offset generally between about 0.08 and 0.12 inches (0.2 and 0.3 cm) and is optimally offset by about 0.106 inches (0.27 cm) from the central axis of the patient end connector 18. This offset coupling of the inspiratory tube receiving connector 96 causes the second end 110 of the inspiratory tube 22 to be generally non-coaxial with the expiratory tube 26 in the area adjacent to the patient end connector 18, although the inspiratory tube 22 is still contained within the interior of the expiratory tube 26, in a generally co-axial relation.

The Applicants have found that this offset coupling, when used with a patient end connector 18 of the type shown in the drawings is valuable, as it helps to provide a more clear, and less resistance causing expiratory flow path in the area 107 (FIG. 14) where the expiratory flow path begins, adjacent to the inspiratory tube receiving connector 96. It was found that this offset arrangement provides better flow characteristics than a more traditional, centered arrangement.

The inspiratory tube receiving connector 96 includes a radially inwardly facing surface 102, that defines the hollow interior passageway 104, that constitutes the distally furthest end of the inspiratory tube passageway of the breathing circuit 10. A radially outwardly facing surfaced 106 is provided for being received by the radially inwardly facing surface 108 of the second (distal) end 110 of the inspiratory tube. As discussed in connection with the expiratory tube, the coupling between the radially inwardly facing surface 108 of the second end (cuff) of the inspiratory tube 110, and the radially outwardly facing surface 106 of the inspiratory tube receiving connector 96 should be a very snug, very secure, and a substantially permanently fixed coupling, to help ensure that a disconnect does not occur between the second end 110 of the inspiratory tube and the inspiratory tube receiving connector 96.

Figure 32:
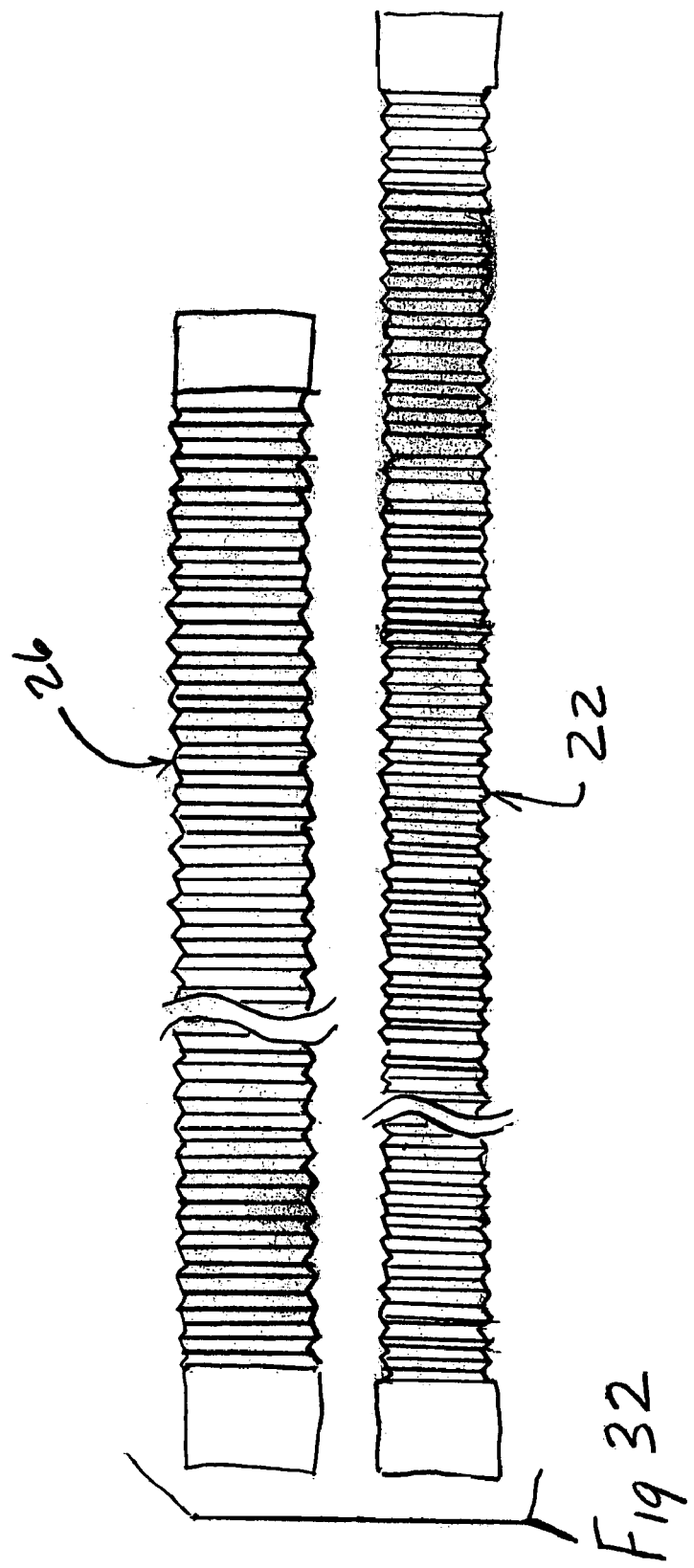
FIG. 32 is a plan view of an inspiratory and expiratory tube placed side by side in their expanded position to show the relative lengths thereof when in their expanded positions.

As a further measure to help prevent disconnects of the inspiratory tube from the machine and patient end connectors, the inspiratory tube is preferably sized to be somewhat longer than the expiratory tube. Preferably, as best shown in FIG. 32, the inspiratory tube, in a standard 44 to 88 inch tube of the type described above, should be between 1 and 7 inches (2.54 to 17.8 cm) longer than the expiratory tube. Optimally, the fully extended length of the inspiratory tube 22 is approximately 4 inches (10.2 cm) greater than the fully extended length of the expiratory tube 26.

This additional length helps to prevent disconnects, by ensuring that when the expiratory tube 26 is pulled to its furthest expanded position, the inspiratory tube 22 still has room to expand. This additional room to expand helps to prevent the imposition of a disconnect inducing stress upon the inspiratory tube, thereby reducing the likelihood of a disconnect of the inspiratory tube 22 from either the patient or machine end connectors.

The reader's attention is now directed to FIGS. 11–19 to gain a better appreciation of the dimensional relationships (where the drawings are expressed in inches) between the various components and parts of the patient end connector 18.

The inspiratory tube 22 and expiratory tube 26 will now be described in more detail, with reference to FIG. 1-9, and FIGS. 27 and 28.

As discussed above, the inspiratory and expiratory tubes are each collapsible, corrugated tubes having a plurality of rest lengths, so that each of the inspiratory and expiratory tubes can be moved from a fully compressed position, to a fully expanded position. Importantly, the inspiratory and expiratory tubes can be selectively expanded and compressed to achieve maintainable rest lengths at a plurality of lengths between the fully expanded and fully compressed positions.

Figure 27:
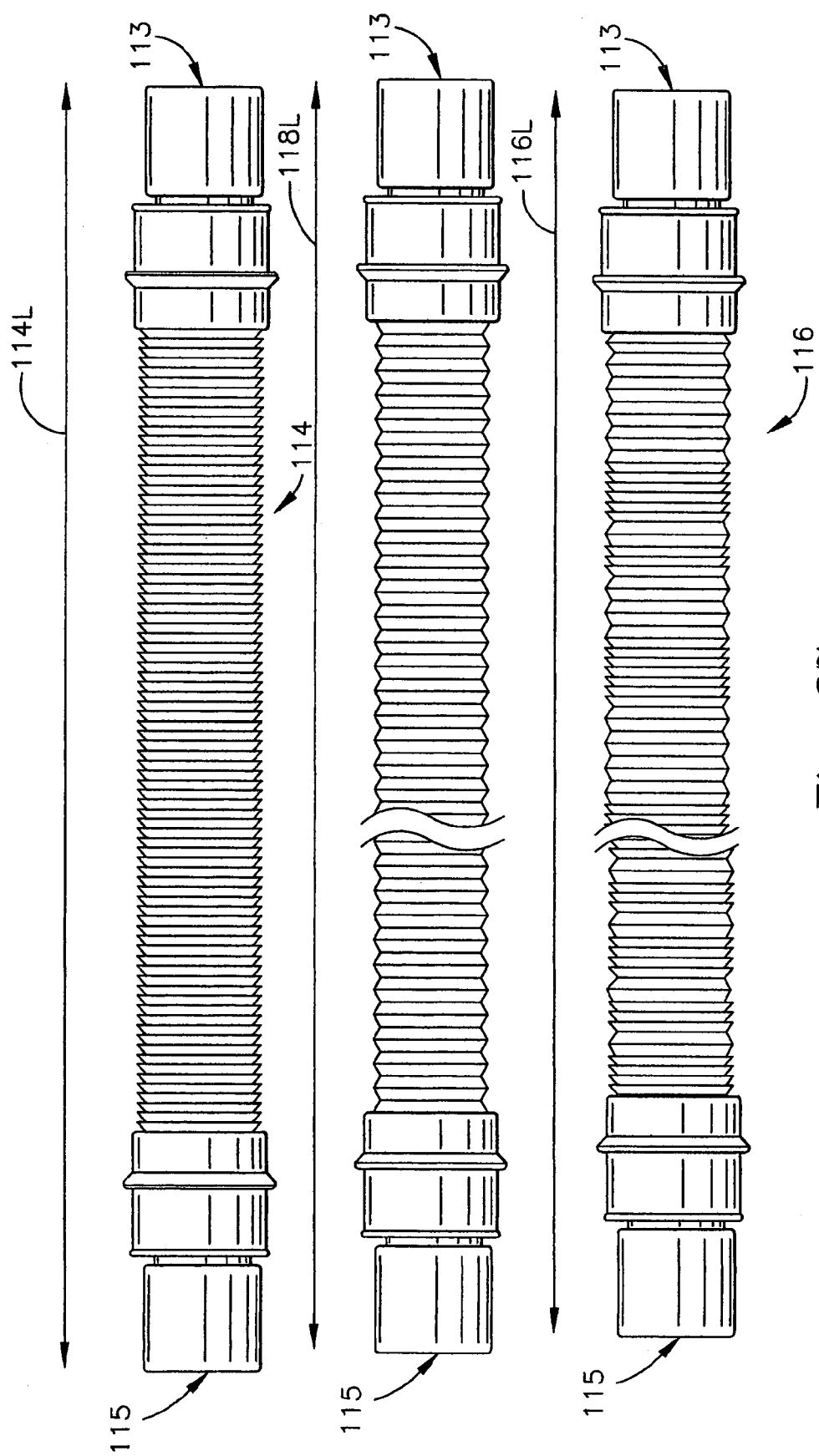
FIG. 27 is a photographic view of three samples of the breathing circuit of the present invention, showing the three circuits in differing states of compression to illustrate the variability of lengths of the circuit.
Figure 28:
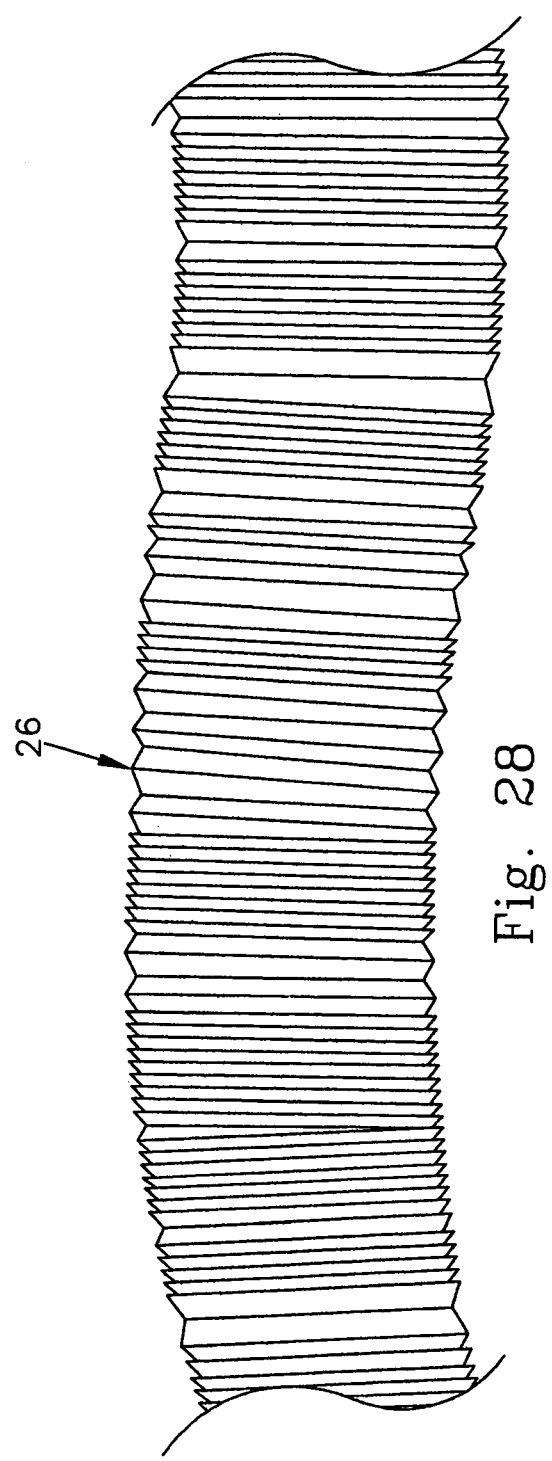
FIG. 28 is a view of the corrugations of the expiratory tube of the present invention.
Figure 29:
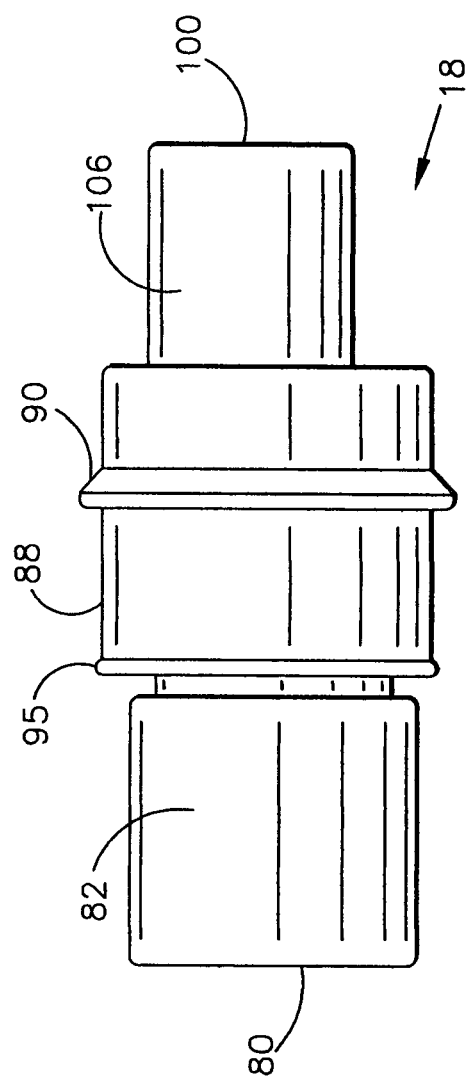
FIG. 29 is a side plan view of the patient end connector of the present invention.

Turning now to FIG. 27, three breathing circuits, including first breathing circuit 114, a second breathing circuit 116 and a third breathing circuit 118 are shown. Although the devices each have inspiratory and expiratory tubes of comparable lengths, their total overall lengths are different due to their different states of compression. It will be noted that each of the three breathing circuits 114, 116, 118 includes a patient end connector 115 and a machine end connector 113. The machine end connectors 113 comprise non-filter bearing machine ends.

The inspiratory and expiratory tubes are generally constructed to have the same length. The first breathing circuit 114 is shown generally in its almost fully compressed position. When in such an almost-fully compressed position, the length 114L of the first breathing circuit is significantly less than the length 116L of the second breathing circuit 116. Additionally, the length 116L of the second breathing circuit is significantly shorter than the length 118L of the third breathing circuit.

The third breathing circuit has a relatively long length 118L that results from most of the the corrugations all being in their expanded position. By contrast, the relatively short length achieved by the first breathing circuit 114L results from most of the corrugations of the inspiratory and expiratory tubes being in their compressed positions. The middle-range length 116L of the second breathing circuit is achieved by a greater percentage of corrugations of the second breathing circuit 116 being in their expanded position, when compared to the shortest breathing circuit 114 and a smaller percentage of the corrugations of the second breathing circuit 116 being in their compressed position, when also compared to the shortened breathing circuit 114.

The purpose of FIG. 27 is to illustrate that the breathing circuit of the present invention can be maintained in a multitude of rest positions, varying from the relatively short position of the first breathing circuit 114 that is achieved by the majority of the corrugations being placed in their compressed position, and the relatively larger length of the third breathing circuit 118, wherein almost all the corrugations are placed in their expanded position.

Preferably, the device is designed so that the difference in length between the fully compressed and fully expanded position can vary by a factor of greater than 3, and preferably 4, so that, when the breathing circuit is in its fully expanded position, it is approximately 3 to 4 more times longer than the length of the breathing circuit when in the fully compressed position.

Returning back to FIGS. 2–4, it will be noted that each of the inspiratory tube 22 and expiratory tube 26 are comprised of a plurality of generally identical corrugations, such as corrugations 120, 122. For purposes of convenience, a corrugation is denoted in this application as a segment of the tube extending between adjacent nadir points 126. Each of the corrugations includes a peak point 124, a first leg 128, disposed on one side of the peak portion 124, and a second leg 130 disposed on the second side of the peak portion 124. The first and second legs each terminate at a nadir point 126 that, for definitional purposes of this application, defines a single corrugation, or corrugation segment.

Turning now to FIG. 6-8, a mold block 150 is employed to make the corrugated expiratory tube as shown. The process by which the tube is made is generally referred to as an extrusion and corrugation molding process, to denote that the tube is first extruded, and then corrugated.

The expiratory tube 26 is manufactured is by first extruding a generally smooth tube having a constant diameter of approximately, 25 mm, in the most preferred embodiment. When the smooth tube emerges from the extruder, it generally has a smooth wall, of constant diameter. Shortly after emerging from the extruder and before the plastic has cooled to below its forming temperature, a series of corrugation-shape containing mold blocks, such as mold block 150 engage the outer surface of the expiratory tube 26, to form the corrugations in the expiratory tube 26. During this process, high pressure air is forced into the interior of the expiratory tube 26, to force the smooth wall of the expiratory tube 26 radially outwardly against the corrugated mold blocks. An exemplary corrugated mold block 150 is shown in the drawings, and is useful for understanding the manner in which the corrugations are formed, since the finished tube (22 and 26, as appropriate) of the present invention will generally conform to the shape of the mold block.

When viewing the mold blocks 150, it is important to remember that the mold blocks engaged the exterior surface of the tube (here, the tube that will emerge, when finished as expiratory tube 26). As such, the point that appears to be a nadir point of the mold block (e.g. point 224 of FIG. 7) is actually a peak point 224, as point 224 will define a shape of a peak point 124 of the finished expiratory tube 26. Similarly, peak point 226 of the mold block (FIG. 7) will define the shape of the nadir point 126 of the finished expiratory tube 26. First leg 228 defines the shape of a first leg 128 of the finished expiratory tube 26, and second leg 230 defines the shape of the second leg 130 of the finished expiratory tube 26 (FIG. 4).

As best shown in FIG. 7, the nadir point 226 of the mold block 150 is rounded, to form a rounded peak point of the finished expiratory tube 26. A sharp corner 231 is placed at the junction wherein the apex point 224 of the mold meets the first leg 228, which corresponds to a peak point of the finished expiratory tube 26.

The construction and shape of the expiratory tube 26 described herein helps to provide it with its collapsibility, and its ability to maintain a rest length in both its expanded and its compressed positions. In this regard, the rounded nadir points formed by form block at nadir points 226 of the mold block (which become peak points of the finished expiratory tube 26, cause the finished tube 26 to contain a plurality of microscopic fissures, when moved between the compressed and expanded position. These microscopic fissures within the plastic of the expiratory tube 226 help to maintain the pleats in their expanded and/or compressed position, as so desired. When in use, it has been found that each pleat, e.g. 120, 122 (FIG. 4) generally is capable of maintaining two rest positions, with one being the frilly expanded position, and the other being the frilly compressed position. As a general rule, the individual pleats do not maintain a rest position at points between their compressed and expanded position.

Viewing the two on a global scale, the plurality of rest positions that can be achieved by the tube is largely a function of the number of particular individual corrugations that are placed in their respective expanded and compressed positions. For example, when the finished tube 26 is fully stretched, most (if not all) of the pleats, e.g. 120, 122 are placed in their expanded position. When the finished tube is in its fully compressed position, most (if not all) of the pleats, e.g. 120, 122 are placed in their compressed positions.

When the finished tube 26 is at an intermediate length between its fully compressed and fully expanded positions, some of the individual pleats, e.g. 120, 122 are placed in their expanded position, where as others are placed in their relatively compressed position.

In this regard, the readers attention is directed in particular to FIG. 8 that shows, when in the expanded position, the first leg 228 of the mold, that forms the first leg 128 of the tube, is disposed at generally an angle of about 40.1 degrees, from a plane that extends generally perpendicular to the axis of the inspiratory tube. Similarly, the second leg 230 of the mold, that forms the second leg 130 of the inspiratory tube, is disposed at about a 46.6 degree angle to a plane disposed perpendicular to the axis of the expiratory tube. Control of the compressibility is also fostered by the fact that the first leg 228 and second leg 230 of the mold block, and hence the first leg 128 and second leg 130 of the finished expiratory tubes are disposed at different angles to the above-discussed hypothetical plane perpendicular to the axis of the expiratory tube 26.

The inspiratory tube is best shown in FIG. 4 as being constructed generally similarly to the expiratory tube 26 insofar as it includes a plurality of individual corrugations, such as corrugations 131, 132. Each of the corrugations, e.g. 131, 132 includes a peak portion 140, a nadir portion 138, a first leg 146 and a second leg 148, that extend between the peak portion 140 and the nadir portion 138. Similar also to the expiratory tube 26, the first and second legs 146, 148 of the inspiratory tube 22 are not identical, but rather, differ slightly. The inspiratory tube 22 is also formed by an extrusion, then corrugation process, similar to the expiratory tube 26. An exemplary mold block of the type that might be employed to manufacture the inspiratory tube 22 is best shown in FIGS. 9 and 10.

When viewing a mold block 161 that is used for the inspiratory tube, it is important to remember that the mold block 161 engages the exterior surface of the inspiratory tube 122, so that portions of the block 161 that form peak points 140 appear as nadir points 238, but will be referred to herein, as peak points 238. Similarly, the points 238 that appear as peak points, actually are forming nadir points 138, and the points that appear as nadir points on the mold block are actually peak points 240, that form peak points 140 of the inspiratory tube.

The overall shape of the mold block 161, and the inspiratory tube formed thereby are generally similar to the mold block 150 and expiratory tube 226, as the nadir points 238 are generally rounded, and form a sharp corner 239, at the intersection of the nadir point 238 and the first leg 244, that cause a sharp corner to be formed in a corresponding position on the inspiratory tube.

It should also be noted that the angle of the second leg 246 and the angle of the first leg 244 are slightly different than the angles used within the expiratory tube 26. It has been found that the second leg 246 is best positioned at an angle of about 49.6 degrees, from a plane disposed perpendicular to the axis of the inspiratory tube 22, and that the first leg is disposed at an angle of about 40.1 degrees from a plane that is disposed generally perpendicular to the axis of the inspiratory tube 22. The angle formed at the peak point, between the first and second legs 244, 246 in the inspiratory tube is greater than the angle employed in the expiratory tube 26. These differences in angles were arrived at after significant experimentation by the applicant, and differ largely due to the differences in size between the inspiratory tube 22 and expiratory tube 26.

As alluded to above, the relative sizing between the inspiratory tube 22 and the expiratory tube 26 proved to be a difficult engineering challenge for the Applicants to achieve. In order to achieve appropriate sizes, Applicants believed it important to ensure that the expiratory passageway 34 between the radially inwardly most point of the expiratory tube, here shown as nadir point 130, and the radially outwardly most point of the inspiratory tube 22, here shown as peak point 140 be great enough so that the expiratory passageway 34 was large enough, to permit expiratory gasses to flow there through with minimal resistence. In this regard, the flow resistance of the breathing circuit should be such that at 60 liters/minute of flow, the pressure drop across the circuit is no more than about 5 cm of water. On the other hand, the difference in size should not be too large, because too large of a gap between the outer surface of the inspiratory tube 22 and the inner surface of the expiratory tube 26 causes difficulties in expanding and retracting the inspiratory tube 22.

As shown in FIG. 3, the Applicants have found that the optimal, maximum outer diameter size for the inspiratory tube 22 is 0.807 inches (2.05 cm), and that the optimal, minimal inner diameter size of the minimal inner diameter of the expiratory tube 26 is 1.076 inches (2.73 cm), to create a donut-shaped expiratory passageway having a width of approximately 0.269 inches (0.68 cm). Of course, it will be appreciated that this 0.269 inch (0.68 cm) diameter will not be maintained at all places, at all times, along the entire length of the inspiratory and expiratory tubes 22, 26, as the flexible nature of the tubes 22, 26 will cause the relative position of the expiratory and inspiratory tubes to vary along the length of the inspiratory and expiratory tubes 22, 26. Nonetheless, this gap represents an average gap distance between the expiratory tube 26 and inspiratory tube 22.

As will be appreciated, another way of viewing the optional sizing of the expiratory and inspiratory tubes is that the ratio of the mean outer diameter of the inspiratory (inner) tube ("MODIT") (here, 0.807 inches (2.05 cm)) to the mean inner diameter of the expiratory (outer) tube ("MIDET") (here, 1.076 inches (2.73 cm)) is about 0.75. Although a MODIT to MIDET ratio of about 0.75 is optimal, the Applicants have found that a MODIT/MIDET ratio in the range of between about 0.65 and 0.85 will generally work acceptably.

It will also be noted that the difference between the MIDET and MODIT is optimally about 0.27 inches (0.69 cm), and is believed to be preferably in the range of between about 0.25 and 0.29 inches (0.63 and 0.74 cm). A more preferable range is believed to be between about 0.26 and 0.28 inches (0.66 and 0.72 cm).

An alternate embodiment patient end connector 300 is shown in FIGS. 22–26. Patient end connector 300 includes a patient device receiving portion 302 and a tube receiving portion 304. The patient device receiving portion is configured generally similarly to the patient device receiving portion of the primary embodiment patient end connector 18 shown in FIG. 11, and includes an interior cylindrical connector member 308, and an exterior cylindrical connector member 310, that are separated by a distance to define a cylindrical slot 312 therebetween. A gas receiving port 314 is defined by the radially inwardly facing surface of the interior cylindrical connector member 308.

The tube receiving portion 304 includes a radially outwardly facing surface 316, for snugly, fixedly being received by the radially inwardly facing surface 318 of an expiratory tube 26 (FIG. 25). A radially outwardly extending circumferential spike 302 is formed in the radially outwardly facing surface 316, and is sized and positioned to mate with a receiving ring 321 of the expiratory tube 26 to snugly and fixedly hold the expiratory tube 26 onto the patient end connector 300.

An inspiratory tube receiving connector 324 is also provided. The inspiratory tube receiving connector 324 is configured somewhat differently than the corresponding inspiratory tube receiving connector of the patient end connector 18 shown in FIG. 11. One primary difference is that the inspiratory tube receiving connector 324 of patient end connector 300 is disposed relatively coaxially with the remainder of the patient end connector 300.

The inspiratory tube receiving connector 324 includes a distal end 326 that is unitarily formed with, and attached to the patient device receiving portion 302 of the patient end connector 300. The inspiratory tube receiving connector 324 also includes a proximal end 328 that may include a relatively larger diameter, radially outwardly extending end lip 329. Similar to spike 320, lip 329 helps to securely hold the inspiratory tube onto the inspiratory tube connector 324. The inspiratory tube receiving connector 324 includes a radially outwardly facing surface 330 for snugly engaging, and being received by the radially inwardly facing surface 333 of the distal end 331 of the inspiratory tube 22. The inspiratory tube connector portion also includes a radially inwardly facing surface 332 that defines the inspiratory gas passageway 334.

An important distinction between patient end connector 300, and patient end connector 18 (FIG. 11) is the presence of apertures 336 that are disposed adjacent to the distal end 326 of the inspiratory tube connector 324. The apertures 328 permit gas to flow between the gas port passageway 314, and the expiratory passageway 334. Primarily, the gas that will travel through apertures 338 constitutes expired gas, that is being exhaled. The gas travels in a direction within the patient end connector indicated generally by arrow J and then travels outwardly through the arrows K (FIG. 25), into the expiratory gas passageway 34, ultimately traveling back to the anesthesia machine. The apertures 336 should be sized, as indicated within the drawings, to accommodate a relatively low resistance flow of expiratory gas through the apertures 336 and into the expiratory gas passageway 334.

Figure 30:
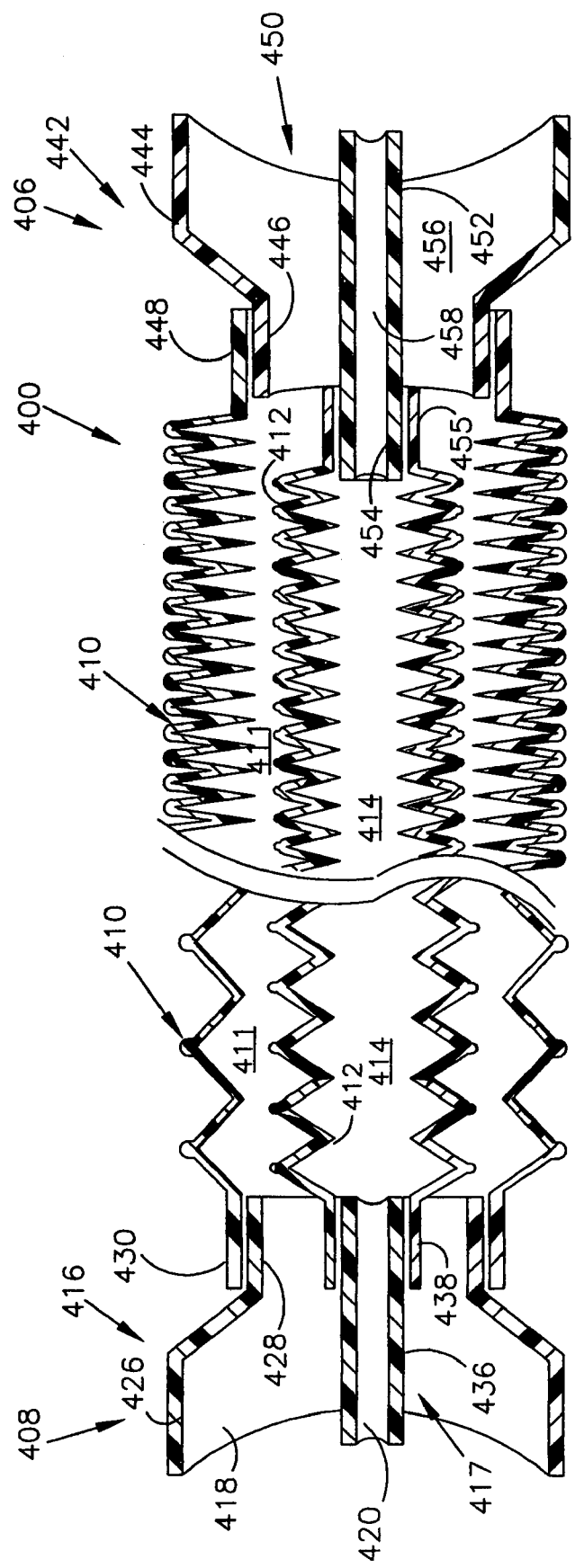
FIG. 30 is a side, sectional view of a second alternate embodiment breathing circuit showing the present invention employed in an extension circuit type breathing circuit.

An alternate embodiment breathing circuit 400 is shown in FIG. 30. Breathing circuit 400 comprises an extension type breathing circuit of the type that can be used to extend the effective length of a breathing circuit such as the UNIVERSAL F2® type breathing circuit.

For example, the extension type breathing circuit 400 can be used in connection with breathing circuit 10 shown in FIG. 1, with the two being placed in an end-to-end relationship, wherein the male (patient end) connector 406 of extension type breathing circuit 400 is coupled to the female end connector 40 of breathing circuit 10. The extension type breathing circuit 400 is useful in situations wherein space or other considerations require a breathing circuit that is longer than the length (even when fully extended) of the breathing circuit 10 that was either manufactured by the manufacturer or stocked by the hospital.

The extension type breathing circuit 400 comprises a variable rest length breathing circuit that includes a male (patient end) connector 406, that is coupled to the breathing circuit 10 and a female (machine end) connector 408, that is designed to receive the patient (distal end) of a proximal terminal that itself is coupled to an anesthesia machine. The breathing circuit 400 includes a variable rest length expiratory tube 410 that defines an expiratory passageway 411 that extends through the circuit, and a variable rest length inspiratory tube 412, that defines an inspiratory passageway 413 therein.

In construction and configuration, the expiratory tube 410 and inspiratory tube 412 are generally similar to the expiratory tube 26 and inspiratory tube 22 shown in connection with the embodiment in FIG. 1. Both the inspiratory tube 412 and expiratory tube 410 are constructed to have variable rest lengths, so that the overall rest length of the circuit 400 is variable from a relatively compressed position, as shown on the left side of FIG. 30, and a relatively expanded position, as shown on the right side of FIG. 30. The relative sizes of the inner and outer diameters of the expiratory tube 410 and inspiratory tube 412, respectively, and the considerations employed in sizing and configuring the expiratory and inspiratory tubes 410, 412 are also generally similar to those same considerations, sizes and configurations discussed above in connection with the breathing circuit 10 shown in FIG. 1.

The female (machine end) connector 408 includes an expiratory port coupler 416 and an inspiratory port coupler 417, that define an expiratory passageway 418 there between. An inspiratory passageway 420, that is in fluid communication with inspiratory passageway 414 of the inspiratory tube 412 is defined by the interior of the inspiratory port coupler 417. Similarly, the expiratory passageway 418 is in fluid communication with the expiratory port coupler 416.

The expiratory port coupler 416 includes a relatively enlarged diameter proximal terminal expiratory port receiving portion, that is sized and configured for interiorly receiving the expiratory port coupling portion of a proximal terminal, of the type described in Fukunaga U.S. Pat. No. 5,778,872. The expiratory port coupler 416 also includes a relatively reduced diameter expiratory tube receiving portion 428, for exteriorly receiving a cuff 430 disposed at the machine end of the expiratory tube 410. The male (patient end) connector 406, is sized and configured to be coupled to the machine end coupler of a breathing circuit, such as the breathing circuit 10 shown in FIG. 1.

The patient end, or distal connector 406 includes an expiratory port coupler 442 having a circuit engaging portion 444 for being interiorly received by the distal end of the circuit 10, and a relatively reduced diameter expiratory receiving portion 446, that is sized and configured for being received by the distal end cuff 448 of the expiratory tube 410. The inspiratory port connector 450 includes a circuit engaging portion 452, that is designed to be interiorly received within the inspiratory tube connector of the circuit 10. The inspiratory port connector 450 also includes an inspiratory tube receiving portion 454, that is designed for receiving a cuff 455 located at the distal end of the inspiratory tube 412.

An expiratory passageway 456 of the coupler is defined between the expiratory port coupler 442 and the inspiratory port coupler 450, and is in fluid communication with the inspiratory passageway 411. Similarly, an inspiratory passageway 458 is defined by the interior of the inspiratory port coupler 450, and is in fluid communication with the inspiratory passageway 414 of the inspiratory tube 412.

Similar to the other circuits discussed above, circuit 400 is moveable between a compressed and an expanded position, and can assume any of a variety of different rest lengths, due to the variable rest length capability of the inspiratory and expiratory tubes 410, 412. It should be noted that both ends 438, 455 of the inspiratory tube 412 of circuit 400 are preferably centered within their respective expiratory couplers 408, 406. A radially offset mounting, such as that shown in connection with the patient end of the circuit 10 of FIG. 1 is not needed. Rather, the inspiratory tube should be centered to facilitate mating with both the proximal terminal and the proximal end of the breathing circuit 10.

Figure 31:
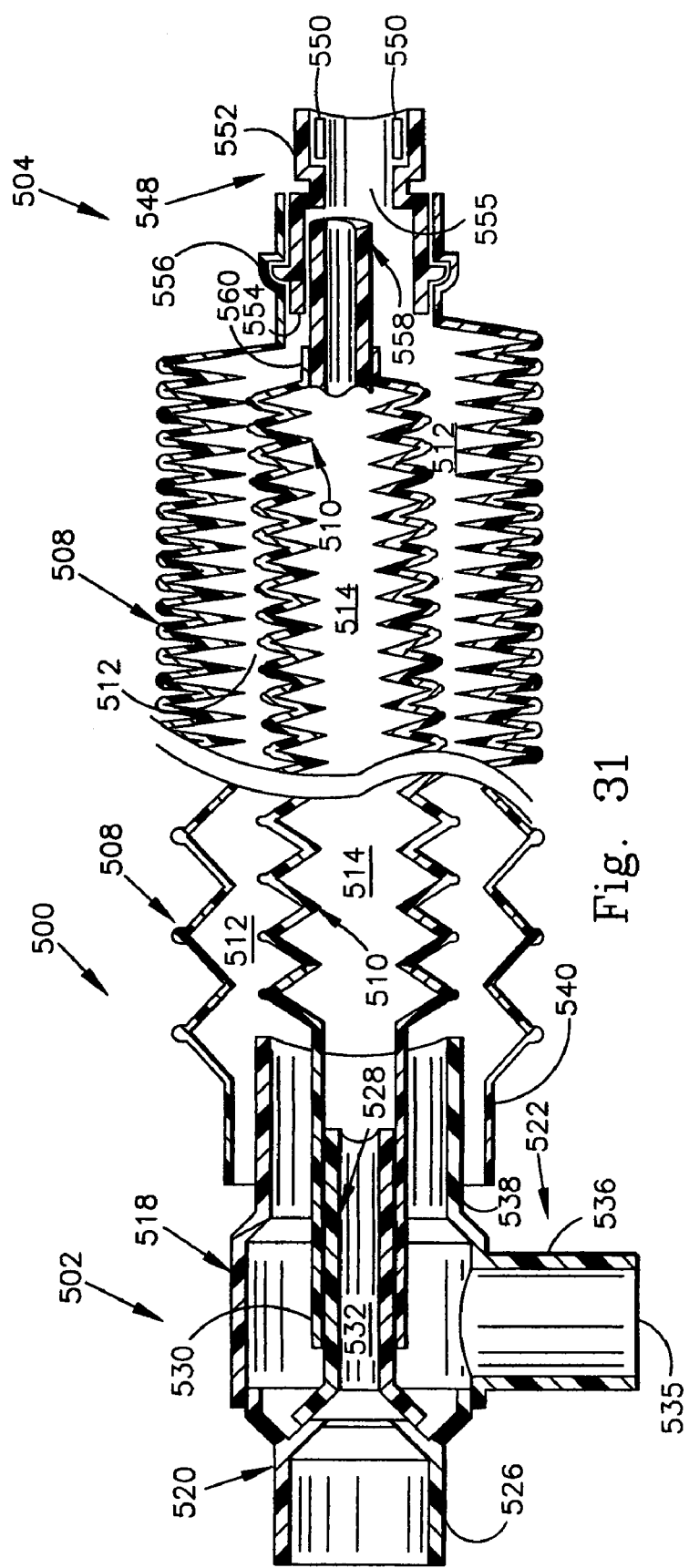
FIG. 31 is a side sectional view of a third alternate embodiment breathing circuit showing the present invention employed in a breathing circuit having separated non-coaxial machine end inspiratory and expiratory ports.

FIG. 31 shows an second alternate embodiment breathing circuit 500, that includes a machine end 502 that is generally similar to the machine end of the breathing circuit shown in the Leagre and Burrow U.S. Pat. No. 5,404,873, and a patient end 504, that is generally similar to the patient end 18 shown in FIG. 1 herein. The machine end 502 and patient end 504 are used in connection with a variable rest length expiratory tube 508, and a variable rest length inspiratory tube 510 of the present invention.

The expiratory tube 508 and inspiratory tube 510 are constructed generally similarly to the expiratory tube 26 and inspiratory tube 22 shown in FIG. 1. Both 508, 510 comprise accordion type tubes containing a plurality of pleats, wherein each pleat is movable between an expanded position (such as is shown adjacent to machine end 502), and a compressed position (such adjacent to patient end 504).

The machine end 502 includes a casing 518 having an inspiratory connector 520, and an expiratory connector 522. The inspiratory connector 520 includes an enlarged diameter machine receiving connector member 526, that is sized and configured to be coupled to the appropriate port of an anesthesia machine, or an accessory to an anesthesia machine such as a carbon dioxide absorber. The inspiratory connector 520 also includes a reduced inspiratory tube receiving portion 528 that is sized and configured for exteriorly receiving a cuff 530 of the inspiratory tube 510. The inspiratory connector 520 defines an inspiratory passageway 532 that connects the exterior of the connector 520 to the inspiratory passageway 514 of the inspiratory tube 510.

The expiratory port connector 534 is shown as being separate, and generally not co-axial with the inspiratory connector 520. The expiratory port connector 522 includes an expiratory port 535 that is defined by a hose receiving portion 536 that is sized and configured to be coupled to a hose, that fluidly couples the expiratory port 535 to the appropriate port on an anesthesia machine. The tubing (not shown) couples expiratory port to the anesthesia machine preferably has a sufficient length, and is sufficiently flexible so as to be easily coupleable to the appropriate port on the anesthesia machine. It will be noted, and is discussed in more detail in the Leagre '873 patent, that the connector is designed to maintain the inspiratory and expiratory flow paths separate.

The patient end connector 504, as discussed above, is generally similar to patient end connector 18, shown in FIG. 1, and includes a patient device receiving connector 548 to which a patient device, such as an endo-tracheal tube or a face mask can be coupled. The patient device receiving connector 548 includes an interior cylindrical connector 550 and an exterior cylindrical connector 552, to receive the face mask appropriately. An expiratory tube receiving portion 554 is sized and configured for exteriorly receiving a distal end cuff 556 of the expiratory tube 508. The patient device receiving connector 548 defines a gas port 555, through which both inspiratory and expiratory gases flow.

A radially offset inspiratory tube terminus 558 is radially offset from center, in much the same manner as, and for the same reasons as the inspiratory tube connector 98 of FIG. 1.

The radially offset inspiratory tube terminus 558 includes a proximally disposed portion that is sized and configured for exteriorly receiving a cuff 560 disposed at the distal end of the inspiratory tube 510. The radially offset nature of the inspiratory tube terminus provides a more clear, and less restriction prone passageway, in the area adjacent to the patient end connector 548, to permit expiratory gas that is exhaled by the patient to enter into the expiratory passageway 512, both when the inspiratory and expiratory tubes 510, 508 are in their expanded positions, and when they are in their relaxed positions.

Having described the invention in detail with references to preferred embodiments, it will be appreciated that the above-described invention is not limited by the description herein, but rather, shall be limited only by the claims that shall be attached hereto.

What is claimed is:

1. A unilimb breathing circuit comprising
    a proximal end coupling member
    a distal end coupling member
    a pleated expiratory tube having a first end fixedly coupled to the proximal end coupling member, and a second end fixedly coupled to the distal end coupling member, the expiratory tube being expandable between a fully compressed rest position and a fully expanded rest position, and having a plurality of intermediate rest positions wherein the expiratory tube is capable of maintaining its rest length without the exertion of an external force, and
    a pleated inspiratory tube having a first end fixedly coupled to the proximal coupling member, and a second end fixedly coupled to the distal end coupling member, the inspiratory tube being expandable between a fully compressed position and a fully expanded position, and having a plurality of intermediate rest positions wherein the inspiratory tube is capable of maintaining its rest length without the exertion of an external force,
    wherein the length of the inspiratory tube is greater than the length of the expiratory tube.

2. The unilimb breathing circuit of claim 1 wherein the length of the inspiratory tube is greater than the length of the expiratory tube by between about 1 and 7 inches when each of the inspiratory and expiratory tubes are in their fully expanded positions.

3. The unilimb breathing circuit of claim 1 wherein the length of the inspiratory tube is between about 3 and 5 inches greater than the length of the expiratory tube.

4. The unilimb breathing circuit of claim 1 wherein the length of the breathing circuit in the fully expanded rest position is at least about three time greater than the length of the breathing circuit in the fully compressed rest position.

5. The unilimb breathing circuit of claim 1 wherein the length of the breathing circuit in the fully extended rest position is between about three and four times greater than the length of the breathing circuit in its fUlly compressed rest position.

6. The unilimb breathing circuit of claim 1 wherein the inspiratory tube and expiratory tube are disposed generally coaxially.

7. A re-breathing type unilimb breathing circuit comprising
    a proximal end coupling member having an axis
    a distal end coupling member having an axis
    a pleated expiratory tube having a first end fixedly coupled to the proximal end coupling member, and a second end fixedly coupled to the distal end coupling member, the expiratory tube being expandable between a fully compressed rest position and a fully expanded rest position, and having a plurality of intermediate rest positions wherein the expiratory tube is capable of maintaining its rest length without the exertion of an external force, and
    a pleated inspiratory tube having a first end fixedly coupled to the proximal end coupling member, and a second end fixedly coupled to the distal end coupling member, the inspiratory tube being expandable between a fully compressed position and a fully expanded position, and having a plurality of intermediate rest positions wherein the inspiratory tube is capable of maintaining its rest length without the exertion of an external force,
    wherein the distal end coupling member includes an axis containing terminus for receiving the inspiratory tube, the axis of the terminus being radially offset from the axis of the distal end coupling member.

8. A unilimb breathing circuit comprising
    a proximal end coupling member
    a distal end coupling member
    a pleated expiratory tube having a first end fixedly coupled to the proximal end coupling member, a second end fixedly coupled to the distal end coupling member, an inner diameter and an outer diameter, the expiratory tube being expandable between a fully compressed rest position and a fully expanded rest position, and having a plurality of intermediate rest positions wherein the expiratory tube is capable of maintaining its rest length without the exertion of an external force, and
    a pleated inspiratory tube having a first end fixedly coupled to the proximal end coupling member, a second end fixedly coupled to the distal end coupling member, an inner diameter and an outer diameter, the inspiratory tube being expandable between a fully compressed position and a fully expanded position, and having a plurality of intermediate rest positions wherein the inspiratory tube is capable of maintaining its rest length without the exertion of an external force,
    wherein the ratio of the outer diameter of the inspiratory tube to the inner diameter of the expiratory tube is sized to minimize flow resistance therebetween, while facilitating generally linear compressibility and expandability of the inspiratory and expiratory tubes.

9. The unilimb breathing circuit of claim 8 wherein flow resistance of the breathing circuit is such that at 60 liters/minute of flow, the pressure drop across the circuit is no more than about 5 cm of water.

10. The unilimb breathing circuit of claim 8 wherein the ratio of the mean outer diameter of the inspiratory tube to the mean inner diameter of the expiratory tube is between about 0.65 and 0.85.

11. The unilimb breathing circuit of claim 10 wherein the ratio of the mean outer diameter of the inspiratory tube to the mean inner diameter of the expiratory tube is between about 0.70 and 0.80.

12. The unilimb breathing circuit of claim 10 wherein the size difference between the mean outer diameter of the inspiratory tube and the mean inner diameter of the expiratory tube is between about 0.25 and 0.29 inches.

13. The unilimb breathing circuit of claim 8 wherein the ratio of the mean outer diameter of the inspiratory tube to the mean inner diameter of the expiratory tube is about 0.75.

14. The unilimb breathing circuit of claim 8 wherein flow resistance of the breathing circuit is such that at 60 liters/ minute of flow, the pressure drop across the circuit is no more than about 5 cm of water, and the ratio of the mean outer diameter of the inspiratory tube to the mean inner diameter of the expiratory tube is between about 0.65 and 0.85.

15. A unilimb breathing circuit comprising
a proximal end coupling member
a distal end coupling member
a pleated outer tube having a first end fixedly coupled to the proximal end coupling member, and a second end fixedly coupled to the distal end coupling member, the outer tube including a series of pleats having a first leg and a second leg, the first and second legs being joined to define a series of peak points, the outer tube pleats being expandable between a fully compressed rest position and a fully expanded rest position, and having a plurality of intermediate rest positions wherein the outer tube is capable of maintaining its rest length without the exertion of an external force, the first and second legs of the outer tube pleats being disposed at a first angle when in the compressed rest position, and at a second angle when in the expanded rest position, and
a pleated inner tube having a first end fixedly coupled to the proximal coupling member, and a second end fixedly coupled to the distal end coupling member, the inner tube including a series of pleats having a first leg and a second leg, the first and second legs being joined to define a series of peak points, the inner tube pleats being expandable between a fully compressed position and a fully expanded position, and having a plurality of intermediate rest positions wherein the inner tube is capable of maintaining its rest length without the exertion of an external force, the first and second legs of the inner tube pleats being disposed at a first angle when in the compressed rest position, and at a second angle when in the expanded rest position, wherein the second angle of the inner tube pleats is greater than the second angle of the outer tube pleats.

16. The unilimb breathing circuit of claim 15 wherein the ratio of the outer diameter of the inner tube to the inner diameter of the outer tube is sized to minimize flow resistance therebetween, while facilitating generally linear compressibility and expandability of the inner and outer tubes.

17. The unilimb breathing circuit of claim 16 wherein flow resistance of the breathing circuit is such that at 60 liters/minute of flow, the pressure drop across the circuit is no more than about 5 cm of water, and the ratio of the outer diameter of the inspiratory tube to the inner diameter of the expiratory tube is between about 0.65 and 0.85.

18. The unilimb breathing circuit of claim 17 wherein the length of the inner tube is greater than the length of the outer tube.

19. The unilimb breathing circuit of claim 18 wherein the length of the inner tube is greater than the length of the outer tube by between about 1 and 7 inches when each of the pleats of the inner and outer tubes are in their fully expanded rest positions.

20. The unilimb breathing circuit of claim 19 wherein the distal end coupling member includes an axis containing terminus for receiving the inspiratory tube, the axis of the terminus being radially offset from the axis of the distal end coupling member.

21. The unilimb breathing circuit of claim 15 wherein the length of the inner tube is greater than the length of the outer tube.

22. The unilimb breathing circuit of claim 15 wherein the length of the inner tube is greater than the length of the outer tube by between about 1 and 7 inches when each of the pleats of the inner and outer tubes are in their fully expanded rest positions.

* * * * *